United States Patent
Dai et al.

(10) Patent No.: US 9,119,544 B2
(45) Date of Patent: Sep. 1, 2015

(54) ACQUIRING GLOBAL SHUTTER-TYPE VIDEO IMAGES WITH CMOS PIXEL ARRAY BY STROBING LIGHT DURING VERTICAL BLANKING PERIOD IN OTHERWISE DARK ENVIRONMENT

(71) Applicant: OMNIVISION TECHNOLOGIES, INC., Santa Clara, CA (US)

(72) Inventors: Tiejun Dai, Santa Clara, CA (US); Junzhao Lei, San Jose, CA (US)

(73) Assignee: OmniVision Technologies, Inc., Santa Clara, CA (US)

( * ) Notice: Subject to any disclaimer, the term of this patent is extended or adjusted under 35 U.S.C. 154(b) by 388 days.

(21) Appl. No.: 13/622,976

(22) Filed: Sep. 19, 2012

(65) Prior Publication Data

US 2014/0078277 A1    Mar. 20, 2014

(51) Int. Cl.
| | |
|---|---|
| H04N 7/18 | (2006.01) |
| H04N 5/33 | (2006.01) |
| A61B 1/045 | (2006.01) |
| H04N 5/235 | (2006.01) |
| A61B 1/00 | (2006.01) |
| A61B 1/05 | (2006.01) |
| H04N 5/353 | (2011.01) |
| H04N 5/225 | (2006.01) |

(52) U.S. Cl.
CPC .............. *A61B 1/045* (2013.01); *A61B 1/00004* (2013.01); *A61B 1/051* (2013.01); *H04N 5/2256* (2013.01); *H04N 5/235* (2013.01); *H04N 5/2354* (2013.01); *H04N 5/3532* (2013.01); *H04N 2005/2255* (2013.01)

(58) Field of Classification Search
None
See application file for complete search history.

(56) References Cited

U.S. PATENT DOCUMENTS

| | | | |
|---|---|---|---|
| 4,408,182 A | 10/1983 | Hashimoto et al. | |
| 2002/0080248 A1* | 6/2002 | Adair et al. | 348/230 |
| 2002/0106037 A1 | 8/2002 | Gara | |
| 2005/0094676 A1 | 5/2005 | Iwami et al. | |
| 2006/0066725 A1 | 3/2006 | Dodrill et al. | |
| 2007/0070195 A1 | 3/2007 | Abe | |
| 2007/0159526 A1 | 7/2007 | Abe | |
| 2007/0279486 A1* | 12/2007 | Bayer et al. | 348/65 |
| 2008/0297213 A1 | 12/2008 | Abbasfar et al. | |
| 2009/0216080 A1 | 8/2009 | Nakamura | |
| 2009/0278951 A1 | 11/2009 | Loose et al. | |

(Continued)

OTHER PUBLICATIONS

"Kodak Image Sensors, *Shutter Operations for CCD and CMOS Image Sensors, Innovations in Sight*", Application Note, Revision 3.0 MTD/PS-0259, Jun. 13, 2011, www.kodak.com/go/imagers, 8 pages.

*Primary Examiner* — Jay Patel
*Assistant Examiner* — Reza Aghelvi
(74) *Attorney, Agent, or Firm* — Blakely Sokoloff Taylor & Zafman LLP

(57) ABSTRACT

A CMOS pixel array is introduced into a dark environment to acquire video image frames. During a first frame, each row of pixels is sequentially reset, one row at a time, and then each row of pixels is sequentially read out, one row at a time. During a second frame, each row of pixels is sequentially reset, one row at a time, and then each row of pixels sequentially read out, one row at a time. A light source illuminates the dark environment during a vertical blanking period between the reading of the last row during the first frame and the reading of the first row during the second frame. The light source does not illuminate the dark environment between reading the first and last rows during the first frame nor between reading the first and last rows during the second frame.

23 Claims, 17 Drawing Sheets

(56) References Cited

U.S. PATENT DOCUMENTS

| | | | |
|---|---|---|---|
| 2009/0295959 A1* | 12/2009 | Shoho et al. | 348/294 |
| 2010/0002094 A1* | 1/2010 | Solhusvik et al. | 348/230.1 |
| 2010/0013941 A1 | 1/2010 | Berkey et al. | |
| 2010/0020206 A1* | 1/2010 | Takeda | 348/241 |
| 2010/0060753 A1* | 3/2010 | Yamauchi | 348/241 |
| 2010/0177230 A1 | 7/2010 | Himeno et al. | |
| 2012/0014431 A1* | 1/2012 | Zhao et al. | 375/240.02 |
| 2012/0050550 A1 | 3/2012 | Oba et al. | |
| 2013/0264465 A1 | 10/2013 | Dai et al. | |
| 2013/0264466 A1 | 10/2013 | Dai et al. | |

* cited by examiner

| FIRST VIDEO IMAGE FRAME 835-1 | FIRST VERTICAL BLANKING PERIOD 836-1 | SECOND VIDEO IMAGE FRAME 835-2 | SECOND VERTICAL BLANKING PERIOD 836-2 |
|---|---|---|---|
| (1) TURN OFF LIGHT SOURCE<br><br>(2) NO CHARGE ACCUMULATION SINCE DARK ENVIRONMENT<br><br>(3) READOUT CHARGE ACCUMULATED DURING IMMEDIATELY PRIOR VERTICAL BLANKING PERIOD (NOT SHOWN) USING ELECTRICAL ROLLING SHUTTER | (4) TURN ON LIGHT SOURCE FOR AT LEAST PORTION OF VERTICAL BLANKING PERIOD<br><br>(5) GENERATE AND ACCUMULATE CHARGE WHILE LIGHT SOURCE IS TURNED ON | (6) TURN OFF LIGHT SOURCE<br><br>(7) NO CHARGE ACCUMULATION SINCE DARK ENVIRONMENT<br><br>(8) READOUT CHARGE ACCUMULATED DURING IMMEDIATELY PRIOR VERTICAL BLANKING PERIOD (I.E., FIRST VERTICAL BLANKING PERIOD) USING ELECTRICAL ROLLING SHUTTER | (4) TURN ON LIGHT SOURCE FOR AT LEAST PORTION OF VERTICAL BLANKING PERIOD<br><br>(5) GENERATE AND ACCUMULATE CHARGE WHILE LIGHT SOURCE IS TURNED ON |

FIG. 8

ACQUIRING GLOBAL SHUTTER-TYPE VIDEO IMAGES WITH CMOS PIXEL ARRAY BY STROBING LIGHT DURING VERTICAL BLANKING PERIOD IN OTHERWISE DARK ENVIRONMENT

BACKGROUND

1. Field

Embodiments relate to acquiring images with pixel arrays. In particular, embodiments relate to acquiring images with complementary metal oxide semiconductor (CMOS) pixel arrays.

2. Background Information

FIG. 1 is a block diagram of a known image sensor package 100 that includes an image sensor 101 having a complementary metal oxide semiconductor (CMOS) pixel array 102, control circuitry 103, and readout circuitry 104. Commonly, the CMOS pixel array, the readout circuitry, and the control circuitry are monolithically integrated on a single die or other substrate. The image sensor package provides interconnections (not shown), such as pads, to connect the image sensor with an external signaling medium (e.g., circuitry of a digital camera or other system having the image sensor package).

The CMOS pixel array 102 includes a two-dimensional array of CMOS pixels (e.g., pixels P1, P2, ... Pn). As illustrated, the pixels are arranged in rows (e.g., rows R1 through Ry) and columns (e.g., column C1 through Cx). Commonly there may be anywhere from hundreds to many thousands each of rows and columns of pixels. During image acquisition, the pixels may acquire image data (e.g., photogenerated electrical charges). The image data from all of the pixels may be used to construct an image as is known in the art.

The control circuitry 103 and the readout circuitry 104 are coupled with the CMOS pixel array. The control circuitry is operable to apply electrical signals to the CMOS pixel array to control or assist with controlling aspects of image acquisition. The readout circuitry is operable to read out the image data from the pixels. Commonly, the readout circuitry may read out image data from a single row of pixels at a time along column readout lines 105. The column readout lines are also sometimes referred to as bitlines. The readout circuitry may potentially include amplification circuitry, analog-to-digital conversion (ADC) circuitry, gain control circuitry, or the like. The image data signals 106 may be provided from the readout circuitry to an external signaling medium (e.g., circuitry of a digital camera or other systems having the image sensor package).

The CMOS pixel array 102 commonly uses an electrical rolling shutter. During the image acquisition process, the CMOS pixel array may be exposed to constant and/or continuous light 107 and the electrical rolling shutter may control the amount of exposure that the pixels of the CMOS pixel array are subjected to under the constant/continuous light. For example, in an electrical rolling shutter each row of pixels may be exposed to light during a different period of time in a rolling or sequential fashion. For example, for each acquired image the rows of pixels may be exposed to light sequentially row-by-row from the first row R1 to the last row Ry. As shown, clock signals 108 and rolling shutter image acquisition control signals 109 may be provided to the control circuitry from an external signaling medium (e.g., circuitry of a digital camera or other systems having the image sensor package). The control circuitry may apply electrical signals to the CMOS pixel array based on the received clock and control signals to implement the electrical rolling shutter operations.

FIG. 2 is a circuit diagram illustrating known pixel circuitry 202 for two four-transistor (4T) pixels P1 and P2 of a CMOS pixel array. The pixels P1 and P2 are arranged in two rows and one column and time share a column readout line 205. By way of example, the pixel circuitry may be implemented in the pixels P1 and P2 of the CMOS pixel array 102 of FIG. 1.

Each of the pixels includes a photodiode PD, a transfer transistor T1, a reset transistor T2, an amplifier or source-follower SF transistor T3, a row select transistor T4, and a floating diffusion node FD. Within each pixel, the photodiode is coupled to the floating diffusion node FD by the intervening transfer transistor T1. A transfer signal TX asserted on the gate of the transfer transistor T1 activates the transfer transistor T1. The floating diffusion node FD may represent a circuit node to receive and hold a charge. The reset transistor T2 is coupled between a supply voltage VDD and the floating diffusion node FD. A reset signal RST asserted on the gate of the reset transistor T2 activates the reset transistor T2. The source-follower SF transistor T3 is coupled between a voltage supply VDD and the row select transistor T4. The source-follower SF transistor T3 has a gate coupled to the floating diffusion node FD and a channel selectively coupled to the column readout line 205 through the row select transistor T4. The source-follower SF transistor T3 is coupled to the column readout line when a row select signal SEL is asserted on the gate of the row select transistor T4. The row select transistor T4 selectively couples the output of the pixel to the column readout line 205 when the row select signal SEL is applied to the gate of the row select transistor T4.

FIG. 3 is a plot illustrating timing of known electrical rolling shutter image acquisition control signals that are suitable for implementing an electrical rolling shutter for two rows of a pixel array. Electrical rolling shutter image acquisition control signals are plotted for each of two rows, namely row R1 and row R2, on the vertical axis. Progression of time is plotted from left to right on the horizontal axis. To facilitate description, the electrical rolling shutter image acquisition control signals are described in conjunction with the components and signals of the pixels P1 and P2 of FIG. 2.

Referring to the electrical rolling shutter image acquisition control signals for row R1, the gate of the reset transistor T2 is initially activated by application of a reset signal RST at time t1. While the gate of the reset transistor T2 is activated, a gate of the transfer transistor T1 is pulsed with a transfer signal TX between times t2 and t3. As a result, the photodiode PD and the floating diffusion node FD are reset to the supply voltage VDD. The transfer signal TX is de-asserted at time t3. After the reset, the production and accumulation of photo-generated charges in the photodiode PD begins. The production and accumulation of photo-generated charges in the photodiode PD is also referred to herein as integration. As previously mentioned, there is typically constant/continuous light to expose the photodiode PD throughout the integration. The photodiode PD is operable to generate charges (e.g., photogenerated electrons or holes) in response to such light. As photogenerated charges, for example electrons accumulate on the photodiode PD, its voltage may decrease, since electrons are negative charge carriers (or in the case of photogenerated charges being holes, the voltage may increase accordingly). The amount of voltage or charges accumulated on the photodiode PD may be indicative of the amount and/or intensity of the light incident on the photodiode PD during the exposure period, and may represent image data. For constant intensity light, the longer the exposure period, which is determined by the particular electrical rolling shutter, the more the accumulation of charges.

The reset signal RST may be de-asserted at time t4 to electrically isolate the floating diffusion node FD. A select signal SEL is asserted to the gate of the row select transistor T4 at time t5. This prepares the row R1 of pixels for readout. The gate of the transfer transistor T1 is activated by application of the transfer signal TX between times t6 and t7. This causes the transfer transistor T1 to transfer the photo-generated charges (e.g., electrons) accumulated in the photodiode PD to the floating diffusion node FD. The charge transfer may cause the voltage of the floating diffusion node FD to drop from the supply voltage VDD to a second voltage that is indicative of the image data (e.g., photogenerated electrons accumulated on the photodiode PD during the exposure period). Integration ends upon the finish of the charge transfer. The floating diffusion node FD is coupled to control the gate of the source-follower SF transistor T3. The floating diffusion node FD is presented to the gate of the source follower SF transistor T3. Source-follower SF transistor T3 operates to provide a high impedance connection to the floating diffusion node FD. The source follower SF transistor T3 amplifies the photogenerated charge signal, which is read out to column readout line 205 by row select transistor T4. The row select signal SEL applied to the row select transistor T4 is deactivated at time t8. This completes the readout operation.

As shown, in an electrical rolling shutter, the signals for row R2 each start a predetermined time after the corresponding signals for row R1. That is, each control signal (i.e., RST, TX and SEL) for row R2 is asserted after its counterpart control signal for row R1 has been asserted. The first row R1 is reset, integration is initiated, and then the first row R1 is readout generally a predetermined time after reset. Similarly, the second row R2 may be reset a predetermined time after resetting the first row R1, integration in the second row R2 may be initiated, and then the second row R2 may be readout after the first row R1 has been readout. Notice that integration for row R2 occurs after integration for row R1. It is common that the integration for row R2 starts during the time that the integration for row R1 is taking place. It is noted that the signals in the illustration are not drawn precisely to scale. Such a process may be repeated for all of the other rows of pixels of a CMOS pixel array, sequentially, row-by-row, from the first row R1 to the last row Ry, for each acquired image.

FIG. 4 is a block diagram of a known reset-readout block 410 that represents the reset and readout operations performed when acquiring a single image frame using an electrical rolling shutter. Progression of time 411 is plotted on the vertical axis from top to bottom. The reset-readout block has the shape of a parallelogram. A left vertical side of the parallelogram represents a reset line 412. The reset line is bounded between resetting of the first row R1 (at the top left corner of the parallelogram) through the resetting of the last row Ry (at the bottom left corner of the parallelogram). The intermediate rows between R1 and Ry are reset sequentially row-by-row or one-by-one after the first row R1 though the last row Ry. A right vertical side of the parallelogram represents a readout line 413. The readout line is bounded between readout of the first row R1 (at the top right corner of the parallelogram) through readout of the last row Ry (at the bottom right corner of the parallelogram). The intermediate rows between R1 and Ry are readout sequentially row-by-row or one-by-one after the first row R1 though the last row Ry. The resetting of rows R1 to Ry typically takes the same amount of time as the readout of rows R1 to Ry.

Within an image frame, each row is initially reset and then subsequently read out after a generally predetermined time. The time between the resetting of the row, and readout of that row, represents the exposure period during which the pixels of that row are configured to perform photoelectric charge production and accumulation (i.e., integration). As illustrated by arrow 407, there is typically constant/continuous illumination from at least the resetting of the first row R1 through the readout of the last row Ry. Notice also that the readout of the first row R1 typically begins well before the resetting of the last row Ry. This is typically done to help reduce the overall amount of time needed to acquire an image frame.

BRIEF DESCRIPTION OF THE SEVERAL VIEWS OF THE DRAWINGS

The invention may best be understood by referring to the following description and accompanying drawings that are used to illustrate embodiments. In the drawings:

FIG. 8 is a block diagram illustrating an embodiment of acquiring a sequence of global shutter-type video images using a CMOS pixel array using an electrical rolling shutter in a dark environment.

DETAILED DESCRIPTION

In the following description, numerous specific details are set forth (e.g., specific endoscope systems, specific methods, specific orders of operations, specific timing of illumination, specific rolling shutter image acquisition control signals, specific reset-readout blocks, specific integration/division options for components, etc.) However, embodiments may be practiced without these specific details. In other instances, well-known circuits, structures and techniques have not been shown in detail to avoid obscuring the understanding of the description.

Figure 5:
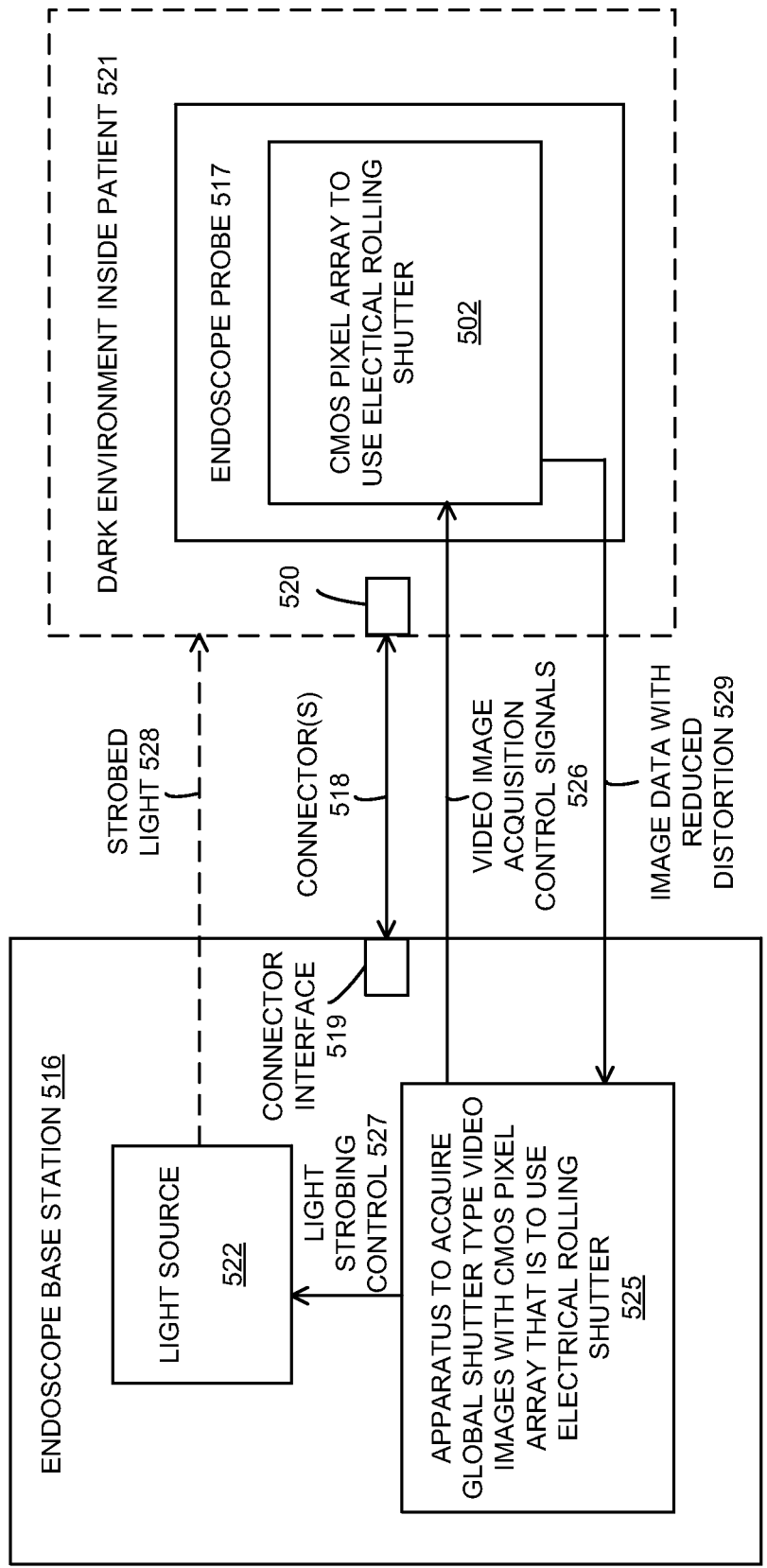
FIG. 5 is a block diagram of an embodiment of an endoscope video image acquisition system.

FIG. 5 is a block diagram of an embodiment of an endoscope video image acquisition system 515. The endoscope video image acquisition system includes an endoscope base station 516, an endoscope probe 517, and one or more connectors 518 to connect or otherwise couple the endoscope probe with the endoscope base station. The endoscope probe and the endoscope base station may represent any of the various different types of endoscope probes and endoscope base stations known in the arts. The scope of the invention is not limited to any known type of endoscope probe or endoscope base station.

Figure 1:
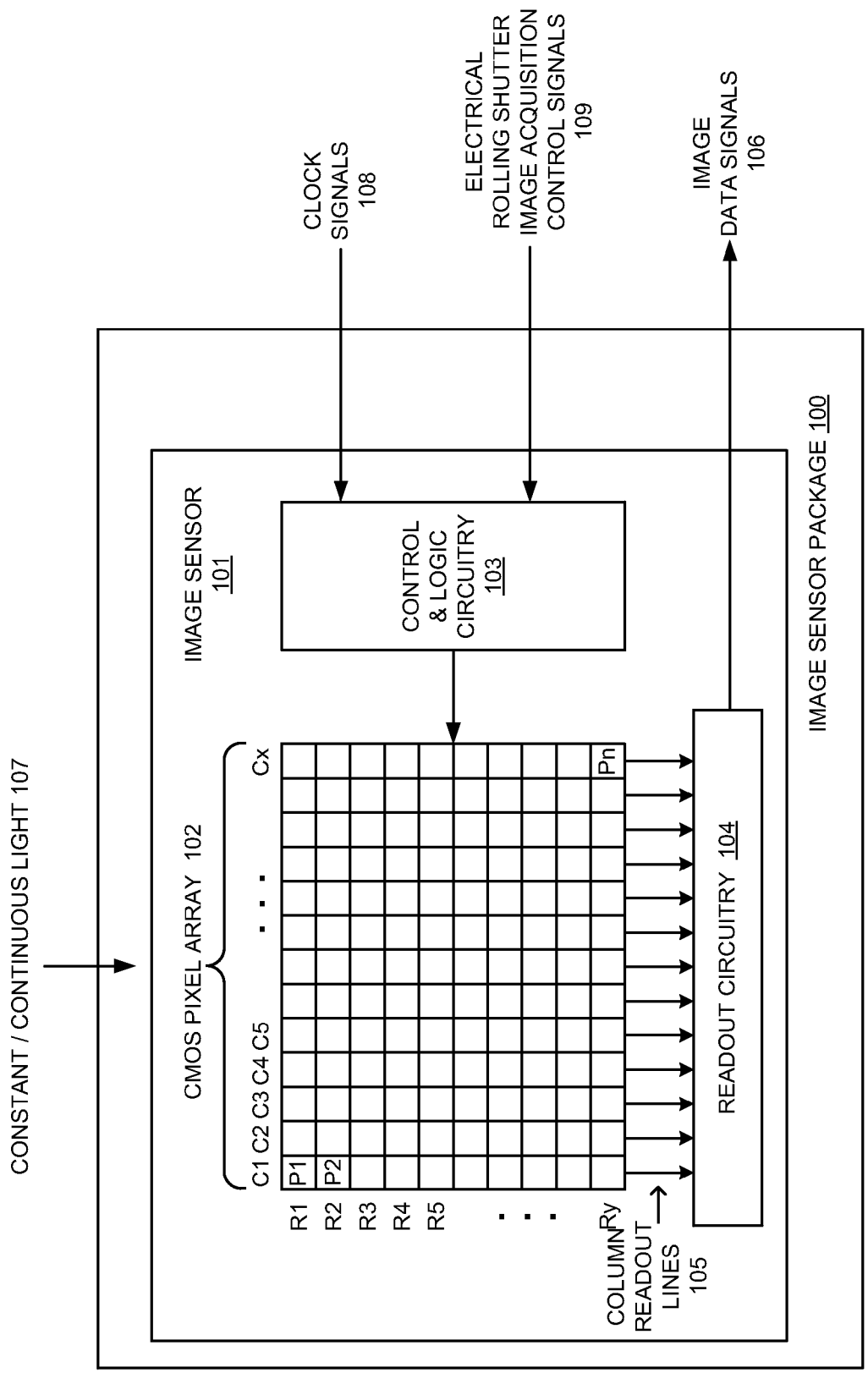
FIG. 1 is a block diagram of a known image sensor package that includes an image sensor having a complementary metal oxide semiconductor (CMOS) pixel array, control circuitry, and readout circuitry.
Figure 2:
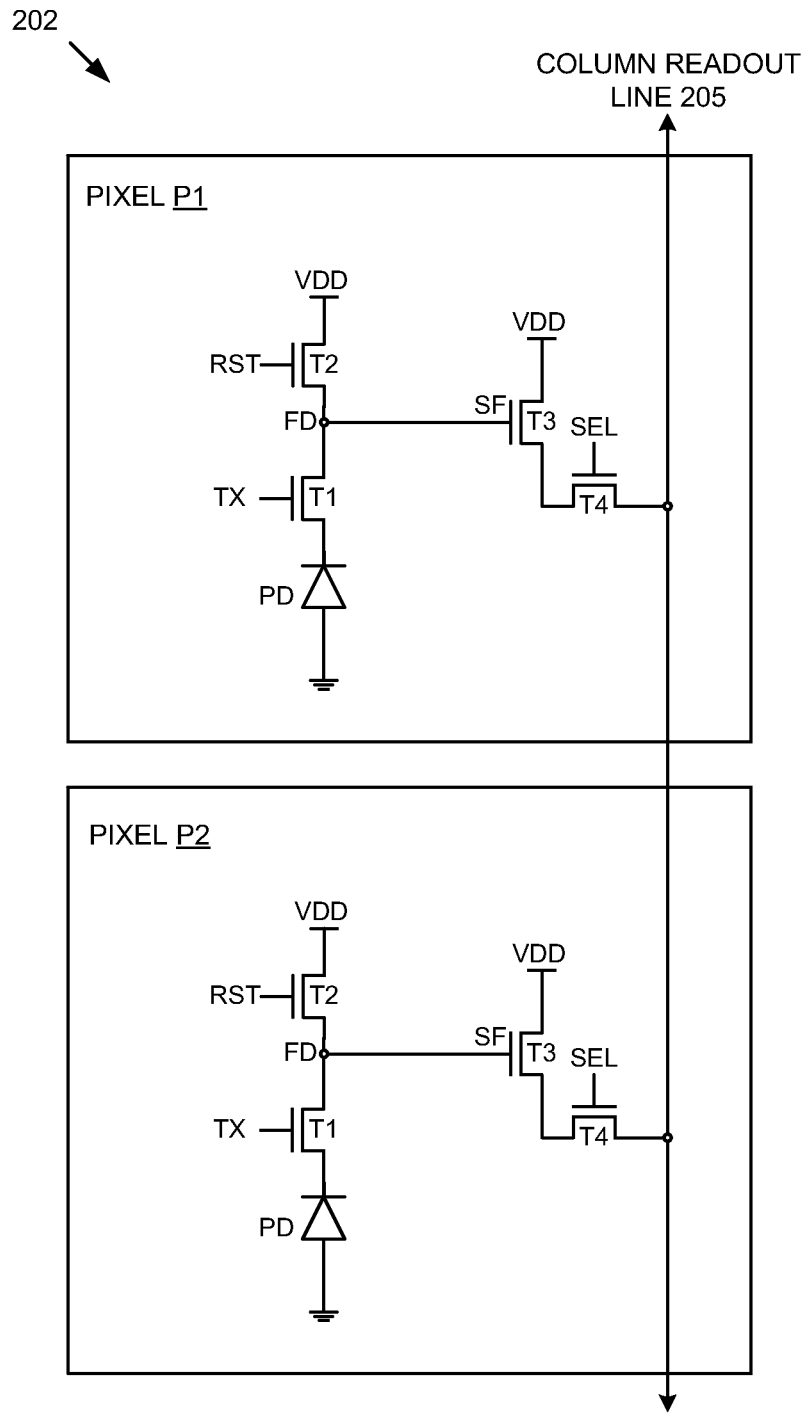
FIG. 2 is a circuit diagram illustrating known pixel circuitry for two four-transistor (4T) pixels P1 and P2 of a CMOS pixel array.
Figure 3:
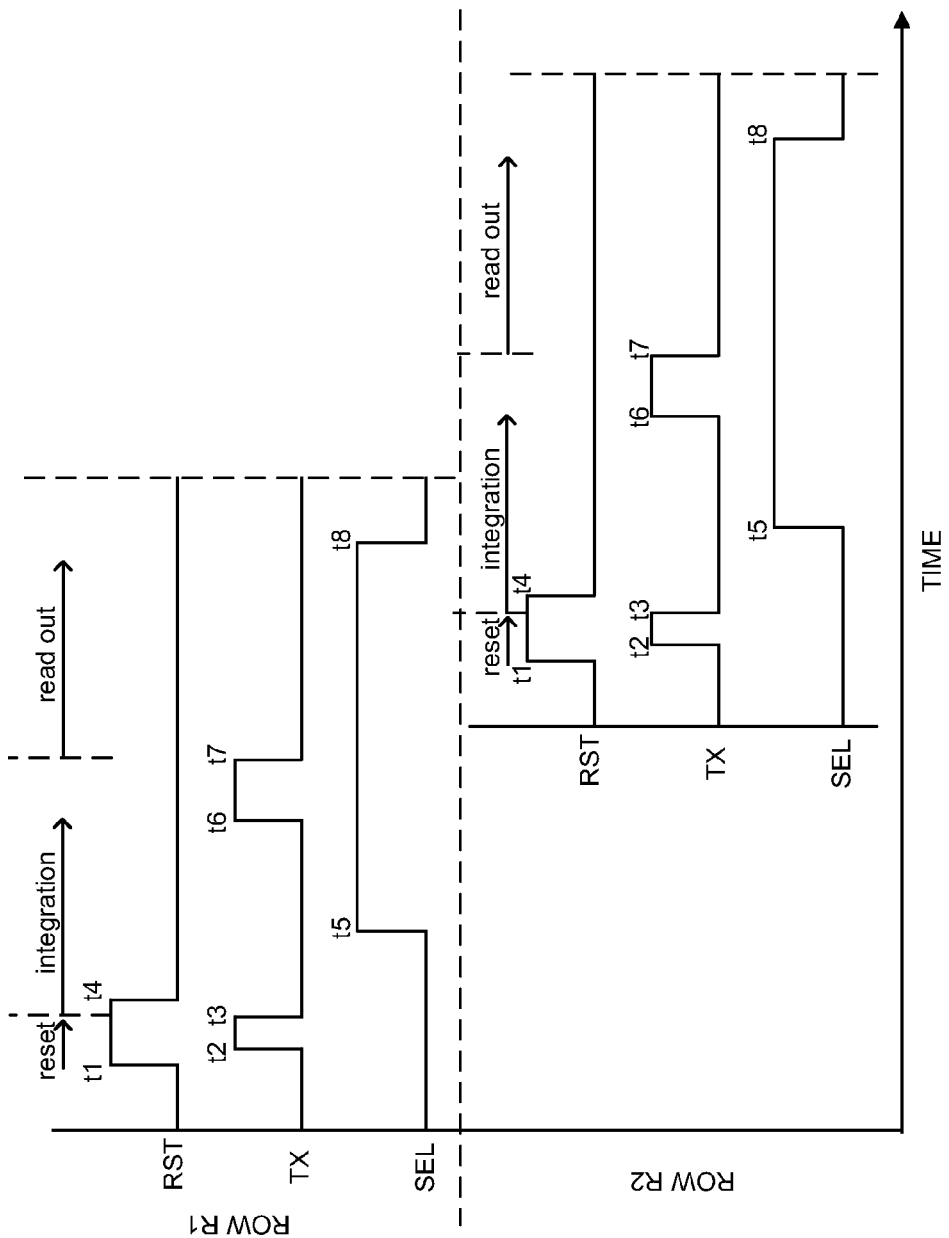
FIG. 3 is a plot illustrating timing of known electrical rolling shutter image acquisition control signals that are suitable for implementing an electrical rolling shutter for two rows of a pixel array.

The endoscope probe 517 often may be a relatively small device that is sized and shaped for insertion into a subject of endoscope examination through various ways known in the art. The endoscope probe includes a CMOS pixel array 502 that is to use an electrical rolling shutter to acquire images. In some embodiments, the CMOS pixel array 502 may be similar to, or the same as, the CMOS pixel array 102 of FIG. 1. Alternatively, a different CMOS pixel array 502 may be used. In some embodiments, the CMOS pixel array 502 may have four-transistor (4T) pixels similar to, or the same as, those shown and described for FIG. 2. Alternatively, different types of pixels may be used.

The endoscope base station 516 often may include an enclosure or housing having therein various different types of components to support the operation of the endoscope probe including operations associated with image acquisition. Examples of different types of components that may be included in the endoscope base station in some embodiments include, but are not limited to, a power supply, clock circuitry, control circuitry, image processing logic, an optional light source (e.g., one or more light emitting diodes (LEDs), lasers, coherent light sources, lamps, etc.), one or more memories, one or more processors, etc. The scope of the invention is not limited to any particular known set of components. The connector(s), such as, for example, one or more flexible cables, may be connected and disconnected between a connector interface 519 of the endoscope base station and a connector interface 520 of the endoscope probe. The connector(s) may house wires or other electrical signaling paths and optical fibers or other optical signaling paths.

The endoscope probe 517 may be used in a dark environment inside the subject of endoscope examination, such as a patient 521. In various different embodiments, the endoscope probe may be inserted into the patient through a native body orifice or opening (e.g., a throat, nose, anus, etc.), through a man-made opening into a body cavity or lumen (e.g., inserted through a surgical opening into a chest, other body cavity, blood vessel, etc.). Such regions within the patient represent dark environments in which there is typically no, or at least insufficient, natural or ambient light, to acquire meaningful images (e.g., images acquired would typically be too dark and/or of insufficient quality to be practically useful for diagnosis or examination). As shown, in some embodiments the endoscope base station may have a light source 522 to provide light to the endoscope probe to help illuminate the dark environment. Alternatively, a light source separate from the endoscope base station may be used (not shown in FIG. 5). As one example, a light source within the endoscope probe (e.g., one or more light emitting devices) may be used. As another example, a stand-alone separate light source not within an enclosure or housing of the endoscope base station may be used. Typically, other than the light provided by the light source, the only natural or ambient light in the dark environment inside the patient 521 is the typically very small amount of light that may get in through the orifice or surgical opening from the external environment where the patient resides.

Once inserted into the patient, the endoscope probe may be navigated, advanced, or otherwise moved within the patient. For example, the endoscope probe may be moved within the patient toward a desired destination (e.g., a region, path, or anatomical feature that is to be examined and/or treated). While the endoscope probe is being moved within the patient, a sequence of video images may be acquired with the CMOS pixel array 502 of the endoscope probe. Without limitation, the video images may potentially be used to help navigate or advance the endoscope probe. Moreover, the video images may potentially also be used for medical examination or diagnosis. In any event, it is generally desirable for the video images to be of sufficiently high quality and to lack significant image artifacts or distortions.

As previously mentioned, the CMOS pixel array is to use an electrical rolling shutter to acquire the video images. One challenge is that image artifacts or distortions may be introduced into the video images that are acquired by using the electrical rolling shutter when there is relative movement between the CMOS pixel array and objects or environments being imaged (e.g., when the CMOS pixel array is being moved within a relatively stationary patient). The distortions and/or artifacts tend to occur due in large part to the different rows of pixels integrating at different times according to the electrical rolling shutter. The movement occurs during the time over which the different rows of pixels integrate within a given image frame. For example, the CMOS pixel array may move relative to a generally stationary object being imaged between the time when the first row of pixels photo-generates and accumulates charge and the time when the last row of pixels photo-generates and accumulates charge within the same image frame such that the first and last rows of pixels may image the object in motion when it is located at different positions. This may cause image artifacts or distortions to appear in the image.

Figure 6:
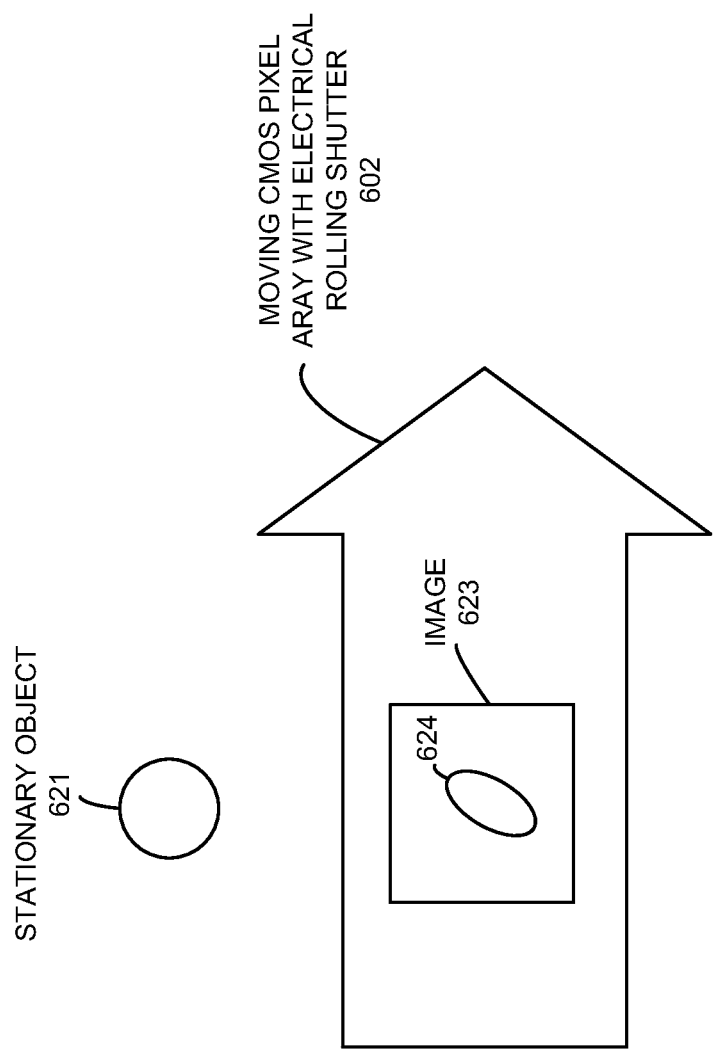
FIG. 6 is a block diagram conceptually illustrating an example of an image distortion that may result when a moving CMOS pixel array using an electrical rolling shutter acquires an image of a stationary object.

FIG. 6 is a block diagram conceptually illustrating an example of an image distortion that may result when a moving CMOS pixel array 602 using an electrical rolling shutter acquires an image 623 of a stationary object 621. The CMOS pixel array 602 is moving from left to right, with respect to the stationary object 621. Alternatively speaking, with respect to the CMOS pixel array 602, the object 621 may be viewed as "moving" from right to left. The illustrated stationary object 621 is a circle. The image acquired with the moving CMOS pixel array using the electrical rolling shutter has a distorted representation of the circle. As shown, the distorted representation of the circle is an oval 624. The top of the oval slants or leans in the direction of movement of the CMOS pixel array. Alternatively speaking, the bottom of the oval slants or leans in the direction of the "movement" of the object 621 relative to the CMOS pixel array 602. As mentioned, this image distortion is largely due to the rows of pixels of the CMOS pixel array integrating at different times while movement is occurring.

One way to avoid, or at least reduce, such image distortions is to use an electrical global shutter. In an electrical global shutter, all of the rows of pixels of the pixel array will integrate simultaneously (e.g., all rows start integration at the same time and all rows end integration at the same time) instead of integrating sequentially row-by-row as in an electrical rolling shutter. In an electrical global shutter, relative movement between the pixel array and the object being imaged will not produce the type of image distortion shown in FIG. 6. Electrical global shutters are common to charge coupled device (CCD) pixel arrays and may also be implemented in CMOS pixel arrays. However, implementing an electrical global shutter in a CMOS pixel array tends to have certain drawbacks. For one thing, one or more additional transistors are generally incorporated in each pixel of the CMOS pixel array in order to help implement the electrical global shutter. For example, each CMOS image sensor pixel may include a reset transistor that receives a global reset signal to reset all photodetectors at the same time to ensure that all the pixels start integration at the same time, and a storage transistor to transfer the photo charges from the photodetectors to floating diffusion at the same time and hold the charges until they are read out later. Such additional transistors tend to increase the size of the CMOS pixel array, which is generally undesirable especially for various endoscope applications. Moreover, these additional transistors also tend to increase the overall manufacturing cost of the CMOS pixel array.

Referring again to FIG. 5, the endoscope base station 516 includes an apparatus 525 that is operable to acquire global shutter-type video images with the CMOS pixel array 502 having the electrical rolling shutter. As used herein global shutter-type video images are those generated with all, or at least a vast majority, of the rows of pixels of the CMOS pixel array integrating concurrently over a same period of time. As used herein, at least a vast majority of the rows of pixels of the CMOS pixel array means at least 90% of the rows of pixels of the CMOS pixel array.

As shown, the apparatus and/or the endoscope base station may provide an embodiment of video image acquisition control signals 526 to the CMOS pixel array and/or the endoscope probe over the connector(s) to cause the CMOS pixel array and/or the endoscope probe to acquire the global shutter-type video images. In some embodiments, the video image acquisition control signals 526 may include electrical rolling shutter video image acquisition control signals. For example, in some embodiments, the signals for each video image may be operable to reset each row of pixels of the CMOS pixel array sequentially, and one row at a time, from a first row to a last row, and to read each row of pixels of the CMOS pixel array sequentially, and one row at a time, from the first row to the last row. In some embodiments, the signals may define, between each pair of consecutive video images, a vertical blanking period that occurs in time between the reading of the last row of pixels of a previous video image and the reading of the first row of pixels of a subsequent video image.

In some embodiments, the video image acquisition control signals are such that, within each video image frame, the resetting of the last row is controlled to be performed before the reading of the first row.

As shown, the apparatus 525 may also provide light strobing control 527 to the light source 522. The light strobing control could alternatively be provided to a light source located outside of the endoscope base station as previously described (e.g., within the endoscope probe or as a separate stand-alone light source outside of the endoscope base station housing/enclosure). The light strobing control may control the light source to provide strobed light 528 to illuminate the dark environment inside of the patient 521. As used herein strobed light refers to light that is intermittently turned on and off, or is turned up or dimmed down, multiple or many times in succession. In some embodiments, the strobed light is only turned on or turned up during at least a portion of each vertical blanking period that occurs between sequential video image frames, and is turned off or dimmed down within each of the video image frames during the periods of time while the rows of pixels are being read out. For example, within a pair of sequential video image frames, the strobed light may be off between the reading/readout of the first and last rows of pixels during an earlier video image frame, may be off between the reading/readout of the first and last rows of pixels during a later video image frame, and may be on during at least a portion of a vertical blanking period between the reading/readout of a last row of pixels of the earlier video image frame and a reading/readout of a first row of pixels of the later video image frame.

As will be explained further below, the strobed light 528 together with the otherwise dark environment inside the patient 521 may effectively cause or result in all, or at least a vast majority, of the rows of pixels of the CMOS pixel array 502 to integrate concurrently over a same period of time, even when an electrical rolling shutter is being used for image acquisition, to allow global shutter-type video images to be acquired. Advantageously, this may help to eliminate, or at least reduce, the amount of image artifacts or distortion that would otherwise tend to occur due to relative movement between the CMOS pixel array and the objects or things that are being imaged. As shown, image data with reduced distortion 529 may be provided from the endoscope probe to the endoscope base station.

Figure 7:
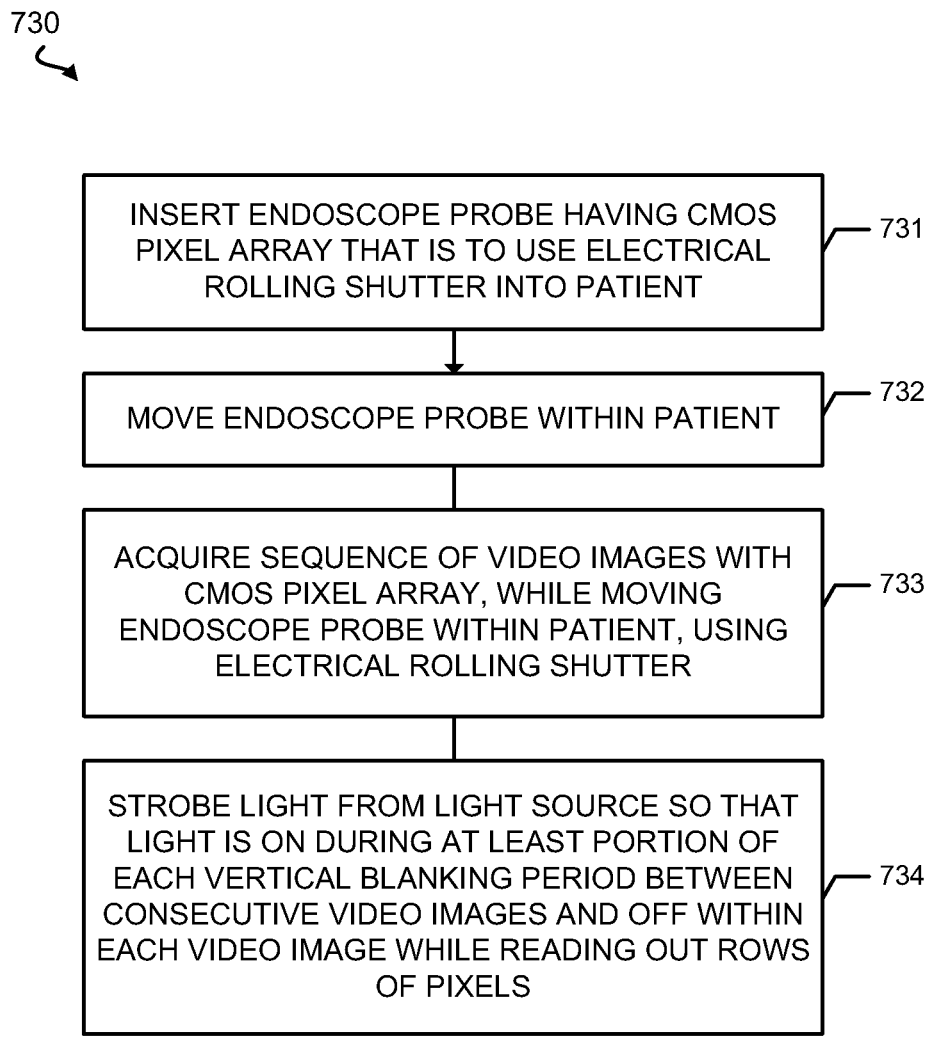
FIG. 7 is a block flow diagram of an embodiment of a method of acquiring global shutter-type video images with an endoscope probe having a CMOS pixel array that uses an electrical rolling shutter.

FIG. 7 is a block flow diagram of an embodiment of a method 730 of acquiring global shutter-type video images with an endoscope probe having a CMOS pixel array that uses an electrical rolling shutter. At block 731, the endoscope probe having the CMOS pixel array that is to use the electrical rolling shutter is inserted into a patient. The endoscope probe is moved within the patient, at block 732. A sequence of video images are acquired with the CMOS pixel array, while moving the endoscope probe within the patient, using the electrical rolling shutter, at block 733. At block 734, light from a light source is strobed so that the light is on during at least a portion of each vertical blanking period between consecutive video images and off within each video image while reading out rows of pixels of the CMOS pixel array. While shown sequentially, blocks 733 and 734 may be carried out concurrently or in parallel to acquire global shutter-type video images with an endoscope probe having a CMOS pixel array that uses an electrical rolling shutter.

FIG. 8 is a block diagram illustrating an embodiment of acquiring a sequence of global shutter-type video images using a CMOS pixel array using an electrical rolling shutter in a dark environment 835. Within a first video image frame 835-1: (1) a light source is turned off (or dimmed down); (2)

no (or very little) charge generation or accumulation occurs since the environment is dark; and (3) a readout of charge accumulated by the CMOS pixel array during an immediately prior vertical blanking period (not shown) occurs row by row from top to bottom. Within a first vertical blanking period, which is subsequent to the first video image frame 836-1: (4) the light source is turned on (or turned up) for at least a portion of the first vertical blanking period; and (5) photoelectric charge is generated (or generated in large amount) and accumulated while the light source is turned on.

Within a second video image frame 835-2, which is subsequent to the first vertical blanking period: (6) the light source is again turned off (or dimmed down); (7) no (or very little) charge generation or accumulation occurs since the environment is dark; and (8) a readout of charge accumulated by the CMOS pixel array during the immediately prior first vertical blanking period 836-1 occurs row by row from top to bottom. Within a second vertical blanking period 836-2, which is subsequent to the second video image frame: (9) the light source is again turned on (or turned up) for at least a portion of the second vertical blanking period; and (10) photoelectric charge is generated (or generated in large amount) and accumulated while the light source is turned on. A subsequent video image frame (not shown) may read out the charge accumulated during the second vertical blanking period. Earlier and subsequent video image frames, and their associated vertical blanking periods, may be similar to those shown.

Figure 9:
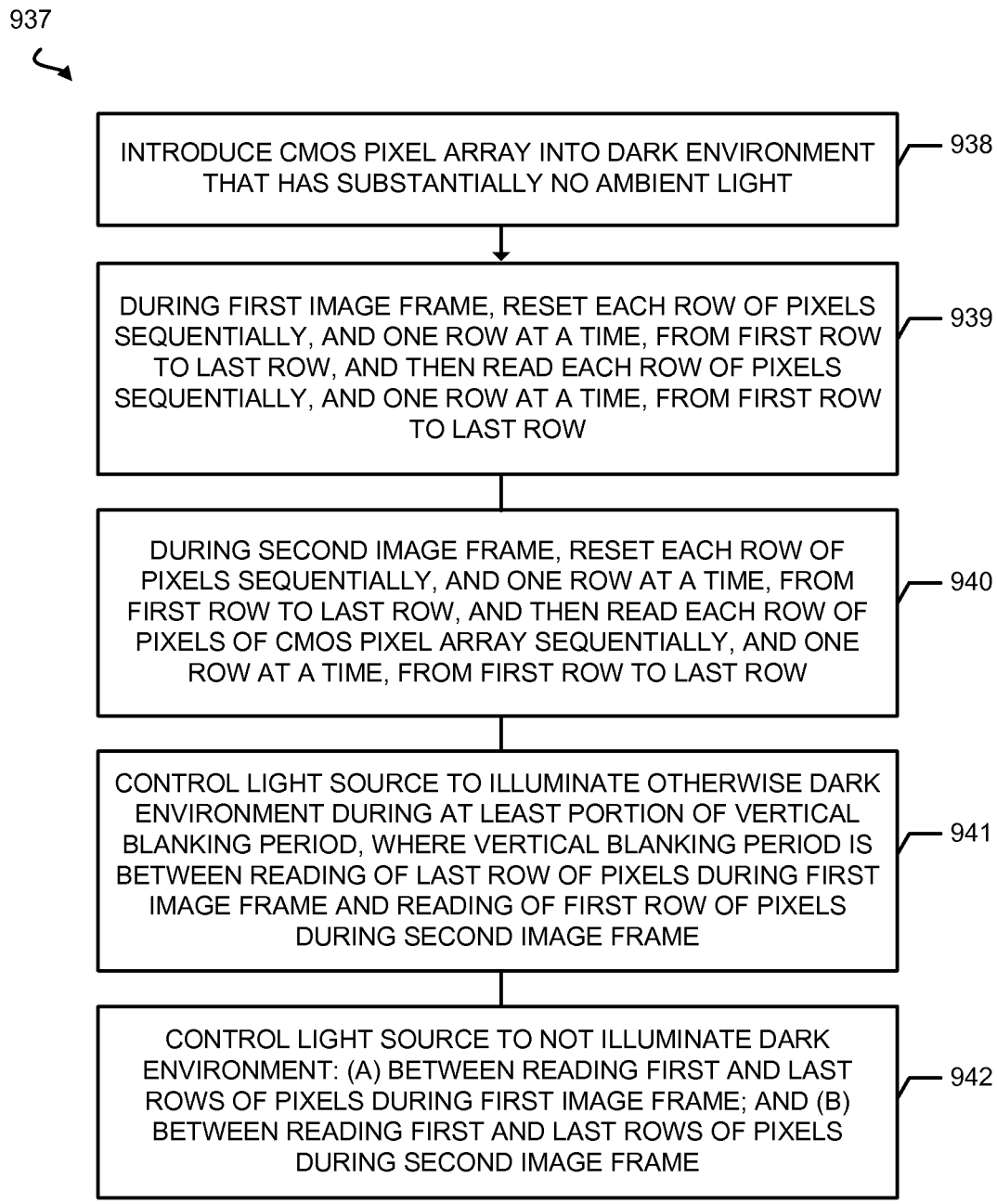
FIG. 9 is a block flow diagram of an embodiment of a method of acquiring a sequence of global shutter-type video images with a CMOS pixel array using an electrical rolling shutter in a dark environment.

FIG. 9 is a block flow diagram of another embodiment showing a method 937 of acquiring a sequence of global shutter-type video images with a CMOS pixel array using an electrical rolling shutter in a dark environment. The CMOS pixel array is introduced into the dark environment at block 938. In some embodiments, an endoscope probe having the CMOS pixel array may be inserted into a patient. Alternatively, in other embodiments, a boroscope, hydraulic pig, or other inspection device having a CMOS pixel array may be inserted into an engine, a tube, a pipeline, or some other dark environment. In some embodiments, the dark environment has substantially no ambient light (e.g., an insufficient amount of ambient light to acquire images that are of sufficient quality to be practically useful). In some embodiments, the dark environment has a darkness value as indicated by a luminance value of less than 1 nit (candela per m$^2$). An even darker environment may have a substantially lower luminance value, for example, $10^{-4}$ nit.

At blocks 939-942, video image frames of the dark environment are acquired with the CMOS pixel array using an electrical rolling shutter. At block 939, during a first video image frame, each row of pixels of the CMOS pixel array is reset sequentially, and one row at a time, from a first row to a last row. Sometime often after the reset of the last row of the CMOS pixel array, integration occurs. See block 941 below, as well as FIGS. 10 and 11, for more detail. Each row of pixels of the CMOS pixel array is then read out sequentially, and one row at a time, from the first row to the last row. Sometime before the readout of the first row of the CMOS pixel array, integration ends. See block 942 below, as well as FIGS. 10 and 11, for more detail. In some embodiments, the resetting of the last row during the first image frame is performed before the reading of the first row during the first image frame.

At block 940, during a second video image frame, each row of pixels of the CMOS pixel array is reset sequentially, and one row at a time, from the first row to the last row. Similar to block 939 above, sometime after the reset of the last row of the CMOS pixel array, integration occurs. Each row of pixels of the CMOS pixel array is then read sequentially, and one row at a time, from the first row to the last row. Similar to block 939 above, sometime before the readout of the first row of the CMOS pixel array, integration ends. In some embodiments, the resetting of the last row during the first image frame is performed before the reading of the first row during the first image frame.

A light source is controlled to substantially illuminate the otherwise dark environment during at least a portion of a vertical blanking period, at block 941. The vertical blanking period is the period between the reading of the last row of pixels during the first video image frame, and the reading of the first row of pixels during the second video image frame. For example, in some embodiments, substantial illumination may include switching on (or turning up) a light source (e.g., switching on or turning up power to one or more LEDs, one or more lasers, one or more coherent light sources, one or more lamps, one or more bulbs, or one or more other light emitting devices). Alternatively, in other embodiments, rather than switching on the light source, a shutter may be opened to allow passage of the light to the dark environment, the light may be reflected, diverted, directed, or otherwise mechanically and/or electrically controlled to be introduced into the dark environment. To substantially illuminate an environment means to provide a luminance that is at least five times more than the luminance when the environment is substantially not illuminated. For example, when an environment is substantially illuminated, the luminance provided is 10 to 100 times more than the luminance when the environment is not substantially illuminated. In another example of substantial illuminating an environment, the light source may be providing a luminous power, i.e., a luminous flux, of approximately 10 to 50 lumen (candela per steradian).

At block 942, the light source is controlled to substantially not illuminate the dark environment between the reading of the first and last rows of pixels during the first video image frame and between the reading of the first and last rows of pixels during the second video image frame. For example, in some embodiments, this may include switching off or turning down a light source. Alternatively, in other embodiments, a shutter may be closed to block passage of the light to the dark environment, the light may be reflected, diverted, or directed away from the dark environment, or otherwise mechanically and/or electrically controlled to not be introduced into the dark environment.

While blocks 939, 940, 941 and 942 are shown sequential, it is to be appreciated that block 941 may occur generally between but potentially partly concurrently with blocks 939 and 940. Moreover, block 942 may occur generally concurrently with block 939 and 940.

In some embodiments, blocks 941 and 942 may include controlling the light source to provide strobed light. The strobed light may substantially illuminate the otherwise dark environment only within sequential vertical blanking periods, but not substantially illuminate the dark environment within video image frames during readout of rows of pixels between the vertical blanking periods.

In some embodiments, substantial illumination with light from the light source occurs only during at least a portion of each of the (or at least some of the) vertical blanking periods. For purposes of illustration, two different possible illumination schemes will be described in detail below. First an "illumination scheme A" embodiment will be described and then later below an "illumination scheme B" embodiment will be described.

Figure 10:
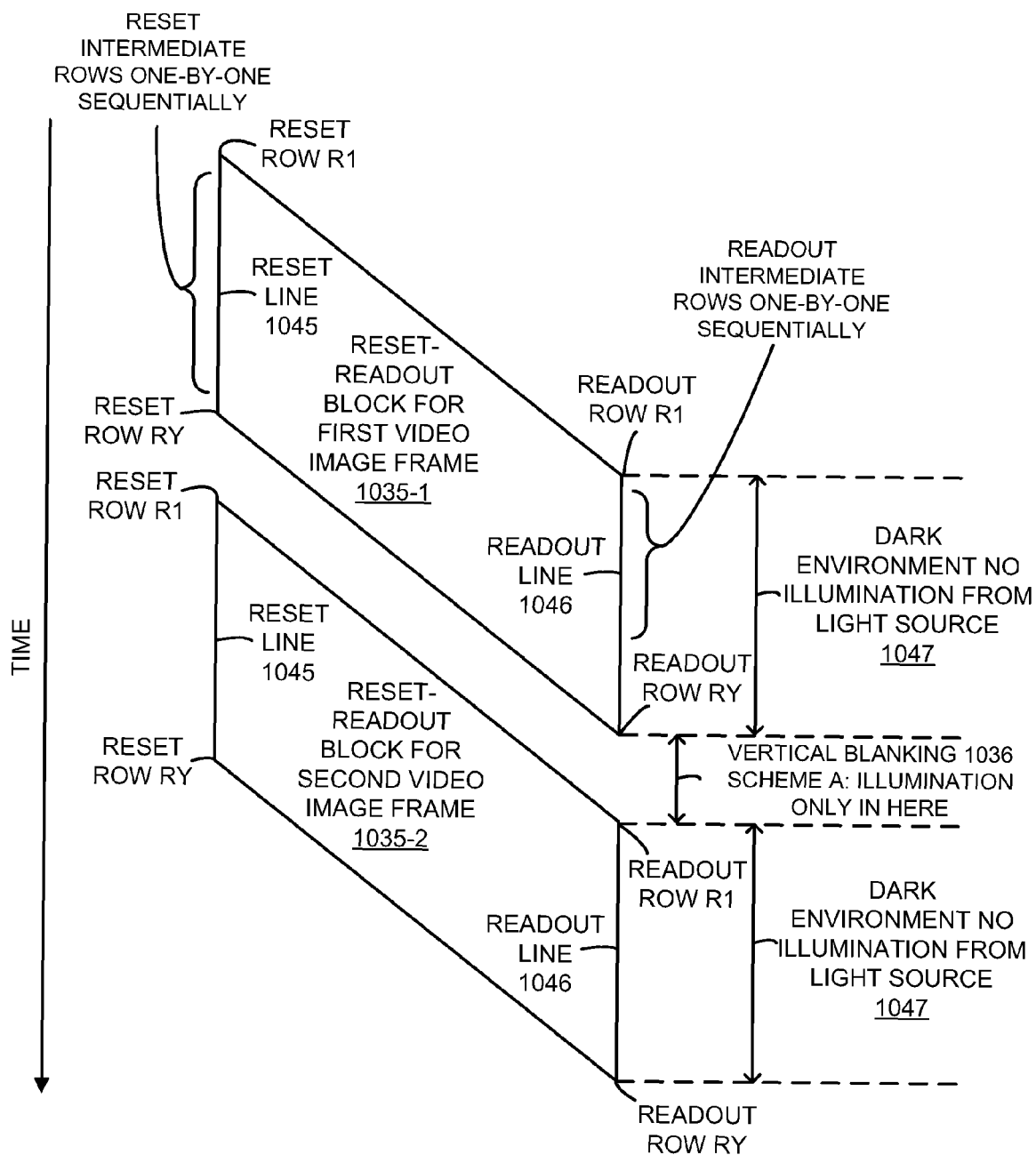
FIG. 10 is a block diagram of reset-readout blocks for consecutive video image frames that illustrate an "illumination scheme A" embodiment in which illumination with light from the light source occurs over potentially the entire and/or over potentially any portion of a vertical blanking period.

FIG. 10 is a block diagram of reset-readout blocks for consecutive video image frames that illustrate an "illumination scheme A" embodiment in which substantial illumination with light from the light source occurs over potentially the entire and/or over potentially any portion of a vertical blanking period 1036. The substantial illumination starts immediately or sometime after start of the vertical blanking period (e.g., immediately or sometime after the last row of pixels is readout in an earlier video image frame) and ends at or sometime before the end of the vertical blanking period (e.g., at or sometime before the first row of pixels is readout during a later video image frame).

As shown on the left side of FIG. 10, progression of time is plotted on the downward-pointing vertical axis from top to bottom. A first reset-readout block 1035-1 for a first, earlier video image frame and a second reset-readout block 1035-2 for a second, later video image frame are shown. Each of the reset-readout blocks has the shape of a parallelogram. A left vertical side of each parallelogram represents a reset line 1045. Each reset line is bounded by resetting the first row R1 (at the top left corner of the parallelogram) through the last row Ry (at the bottom left corner of the parallelogram). Intermediate rows are reset row-by-row or one-by-one sequentially between the first and last rows. A right vertical side of each parallelogram represents a readout line 1046. Each readout line is bounded by readout of the first row R1 (at the top right corner of the parallelogram) through the last row Ry (at the bottom right corner of the parallelogram). Intermediate rows are read out row-by-row or one-by-one sequentially between the first and last rows. Each row is reset before it is subsequently read out at a predetermined later time, with integration occurring after reset and before readout. Resetting from rows R1 through Ry typically takes the same amount of time as readout from rows R1 through Ry.

Figure 4:
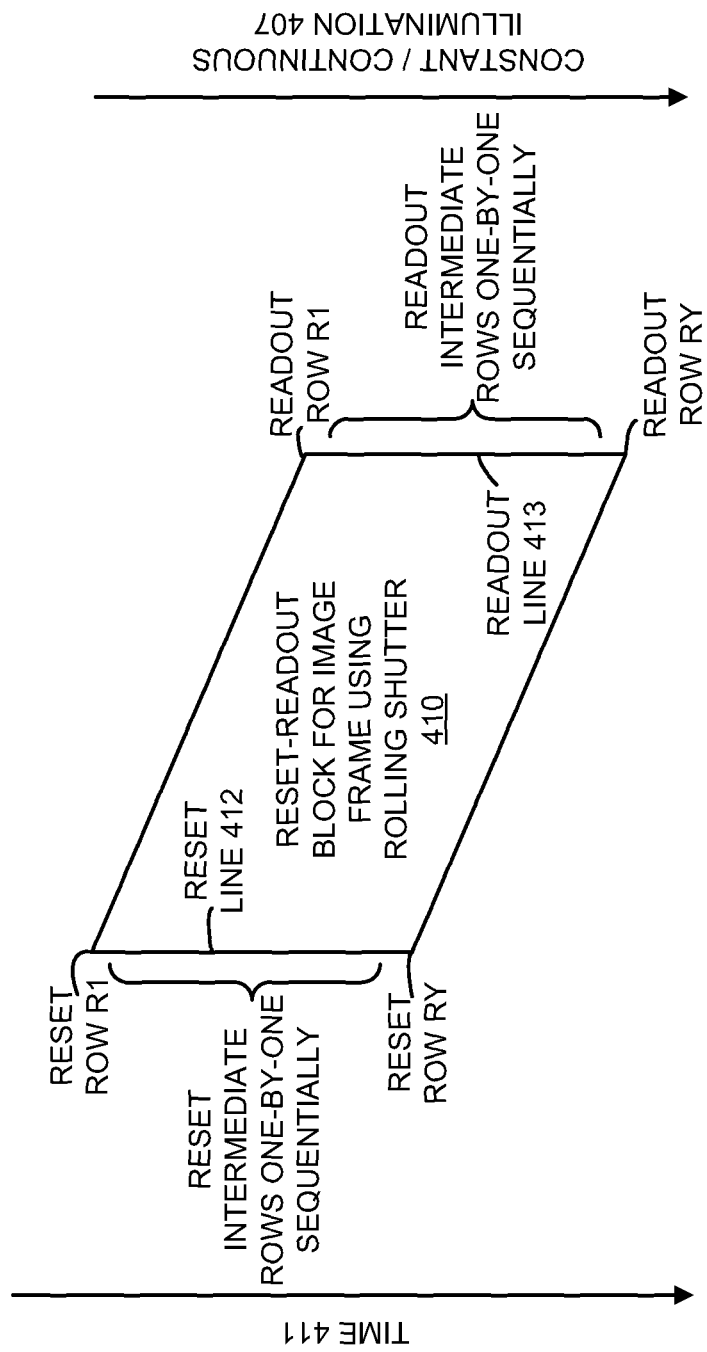
FIG. 4 is a block diagram of a known reset-readout block that represents the reset and readout operations performed when acquiring a single image frame using an electrical rolling shutter.
Figure 11:
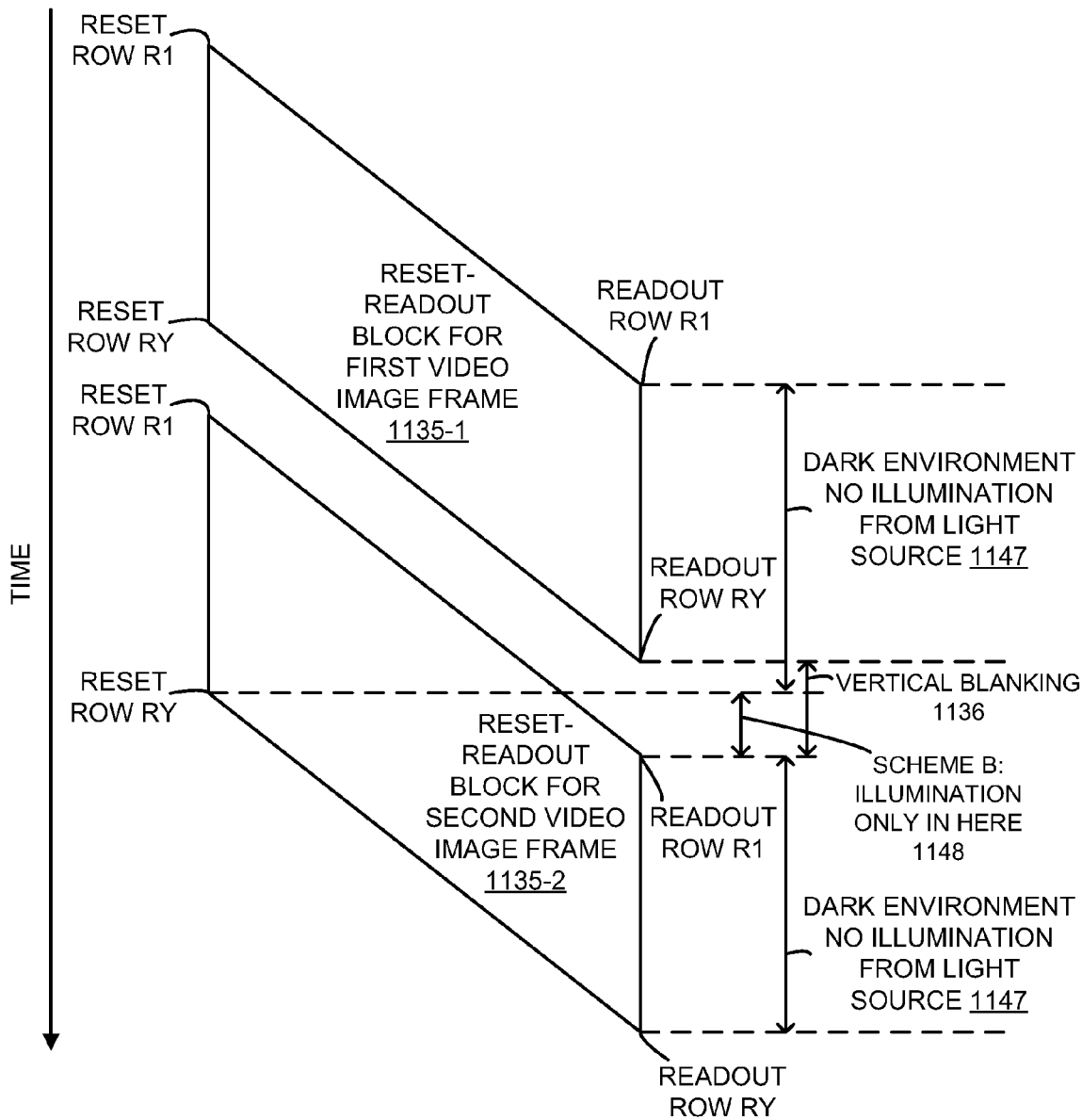
FIG. 11 is a block diagram of reset-readout blocks for consecutive video image frames that illustrate an "illumination scheme B" embodiment in which illumination with light from the light source occurs over potentially an entire and/or potentially any portion of only a post-reset portion of a vertical blanking period.

As shown in FIG. 10, the reset-readout blocks 1035, in some embodiments, the readout of the first row R1 of each video image frame begins after (i.e., is horizontally below) the resetting of the last row Ry within that video image frame. This is different from a prior art reset-readout block 410 as shown in FIG. 4. Referring back to the reset-readout block of FIG. 4, the readout of the first row R1 (at the top right corner of reset-readout block 410 parallelogram) begins well before the resetting of the last row Ry (at the lower left corner of the reset-readout block 410 parallelogram). The reset-readout scheme shown in FIG. 4 reduces the vertical length of the reset-readout block 410, and is done so as to reduce the overall amount of time needed to acquire an image frame and/or to achieve a high video image frame rate, which is typically desired. However, as shown in FIGS. 10 and 11, in some embodiments, resetting the last row Ry of each video image frame before the readout of the first row R1 within the same video image frame offers a potential advantage that all or at least a vast majority of the rows of pixels have been reset and are made ready to begin integration over the same period of time with the strobed illumination light before readout begins, as disclosed herein. This integration timing results in a substantial global shutter-type effect, which is desirable because it substantially overcomes the image distortion caused by the relative motion between the CMOS pixel array and the object that is being imaged.

Notice in FIG. 10 that the reset-readout blocks 1035 have a prolonged integration period, i.e., the period between resetting a given row until reading out the same given row (the vertical distance between the top left corner and the top right corner of the reset-readout blocks 1035 parallelograms), in contrast with the reset-readout block of FIG. 4. Visually, the reset-readout blocks 1035 with a prolonged integration period in FIG. 10 appear to be more vertically elongated than the reset-readout block 410 with a less-prolonged integration period in FIG. 4. The prolonged integration periods may be achieved by resetting a given row (for a second image frame) immediately or relatively soon after reading out that same given row (for a first image frame), such that the readout-to-reset time for the given row is relatively small. Generally, a given imaging cycle for a given row, from resetting the given row in the current imaging frame until resetting the same given row again in the next imaging frame, has fixed time duration. This fixed time duration is the sum of the reset-to-readout time period (e.g., a first vertical distance between the top left corner and the top right corner of the reset-readout block 1035-1 parallelogram) and the readout-to-reset time period (a second vertical distance between the top right corner of the reset-readout block 1035-1 parallelogram and the top left corner of the reset-readout block 1035-2 parallelogram). Reducing or minimizing the readout-to-reset time period (the second vertical distance) helps to increase or maximize the reset-to-readout time period (the first vertical distance). In other words, the integration time is increased or maximized. In some embodiments, after reading out the first row of pixels for the first image frame, the same first row of pixels will be reset for the second image frame within a period of time that is sufficiently short so as to read out no more than about an initial 5% of the rows of pixels of the CMOS pixel array. This helps to prolong the reset-to-readout integration period. However, in other embodiments such prolonged reset-to-readout integration periods are not required.

In the "illumination scheme A" embodiment, illumination with light from the light source occurs over potentially the entire and/or over potentially any portion of the vertical blanking period 1036. In this scheme, illumination with light from the light source does not extend outside the vertical blanking period. For example, the illumination does not occur during the readout of the rows R1-Ry of pixels in either of the bounding video image frames. As shown, within the duration of the readout lines (i.e., the right lines of the two parallelograms 1035) of the bounding video image frames there is a dark environment 1047 with no illumination from the light source. By contrast, in FIG. 4 there is constant/continuous illumination 407 (as represented by the downward arrowed line 407) throughout the entire readout line 413.

Significantly, between being reset and subsequently readout within the same image frame, the rows of pixels are capable of integration. However, due to the dark environment there is no light for integration (or at least insufficient light for any meaningful amount of integration). Only when the light source is controlled to substantially illuminate during the vertical blanking period will any effective integration or at least a vast majority of the effective integration occur. In other words, outside the actual illumination period, even though the time period is still capable of illumination, there is no effective integration due to an absence of lighting or insufficient lighting. As a result, as shown in FIG. 10 and later in FIG. 11, for a CMOS image sensor that operates using an electrical rolling shutter, global shutter-type images can still be obtained, because all or a vast majority of pixels effectively integrate concurrently over the same period of time (e.g., the effective integration starts when the light source is controlled to provide substantial illumination and effectively stops when the light source is controlled not to provide substantial illumination).

Notice that the resetting of the last row Ry in the reset-readout block 1035-2 for the second video image frame (lower left corner of the parallelogram 1035-2) occurs within the vertical blanking period 1036. In other words, after the vertical blanking period begins, and after illumination with light from the controlled light source potentially begins in the "illumination scheme A" embodiment, the last row of pixels Ry is reset to clear the photodetector for subsequent photocharge production. In some embodiments, in addition to the last row of pixels Ry being reset, anywhere up to about 10% of the other rows of pixels immediately above the last row Ry, may also potentially be reset within the vertical blanking period, depending upon the particular timing of the electrical rolling shutters signals of the embodiment. In other words, typically at least the first 90% of the rows of pixels are not reset after the beginning of the vertical blanking period. Accordingly, the last row Ry (and potentially up to about 10% of the other rows immediately above the last row of pixels) have less time for effective integration than about 90% of the other rows below the first row of pixels that are not reset after substantial illumination commences. This will cause some image distortion, but it generally does not cause excessive image distortion, since generally the integration periods tend to be fairly similar, and since generally only a small percentage (e.g., typically up to about 10%) of the other rows above the last row of pixels have the shorter integration period anyway. Generally, the sooner a row of pixels is reset in a subsequent frame after being read out in a previous frame, the less the difference in integration times will be. If desired, the "illumination scheme B" embodiment as disclosed below may be used to avoid such a difference in the integration times as disclosed above in "illumination scheme A".

FIG. 11 is a block diagram of reset-readout blocks for consecutive video image frames that illustrate an "illumination scheme B" embodiment in which illumination with light from the light source occurs over potentially an entire and/or potentially any portion of only a post-reset portion 1148 of a vertical blanking period 1136. The post-reset portion 1148 of the terminal blanking period 1136 occurs after reset of the last row of pixels Ry in the first video image frame 1135-1, proceeding after the onset of the vertical blanking period 1136.

In FIG. 11, a first reset-readout block 1135-1 for a first, earlier video image frame and a second reset-readout block 1135-2 for a second, later video image frame are shown. In the "illumination scheme B" embodiment, illumination with light from the light source starts immediately or sometime after the last row of pixels Ry is reset in a second reset-readout block 1135-2 for the video image frame that follows the onset of the vertical blanking period 1136, and the illumination ends at or sometime before the end of the vertical blanking period 1136 (e.g., at or sometime before the first row of pixels is readout during the second reset-readout block 1135-2 for the second video image frame that follows the vertical blanking period). Notice that in the "illumination scheme B" embodiment, illumination with light from the light source is constrained to occur over only the post-reset portion 1148 of the vertical blanking period 1136 at or after the reset of the last row Ry in the second reset-readout block 1135-2. As a result, the "illumination scheme B" embodiment potentially has slightly less time for integration as compared with the "illumination scheme A" embodiment, due to the lower portion of the dark environment 1147 between the beginning of the vertical blanking period (the second dashed line from the top at the right side of FIG. 11) and the resetting of the last row of pixels Ry (the third dashed line from the top at the right side of FIG. 11) occupying the initial, upper portion of the vertical blanking period 1136.

Since in the "illumination scheme B" embodiment, illumination begins at or after the last row of pixels Ry is reset, all of the rows of pixels of the pixel array have the same integration period. This may help to provide slightly less distorted video images. No rows of pixels (e.g., including the last row of pixels Ry) integrate over shorter periods of time than other rows of pixels. Rather, all rows of pixels integrate over the same period of time. Recall from above that this may not be the case for the last set of up to about 10% of the rows of pixels in the "illumination scheme A" embodiment. Accordingly, the "illumination scheme B" embodiment may provide somewhat more accurate or less distorted images than the "illumination scheme A" embodiment. Although, the "illumination scheme A" embodiment may very closely approximate the accuracy of the "illumination scheme B" embodiment for almost all rows of pixels when each row of pixels is reset in a subsequent frame very soon after it is read in a prior frame. In such cases, the "illumination scheme A" embodiment may offer an advantage over "illumination scheme B" embodiment by allowing illumination to be coordinated based on readout signals only (e.g., the readout signal of the last row Ry for the first image frame and the readout signal of the first low R1 for the second image frame, as shown in FIG. 10). In contrast, both the reset signal of the last row Ry for the second image frame and readout signal of the first row R1 for the second image frame can be used to coordinate illumination for the "illumination scheme B embodiment", as shown in FIG. 11.

For simplicity, a few example illumination scheme embodiments have been described in detail above. Other illumination scheme embodiments are also contemplated. For example, other illumination scheme embodiments may optionally end prior to the end of the vertical blanking period. As another example, other illumination scheme embodiments may use only a central portion of the vertical blanking period not as strictly tied to the timing of the reset and readout lines. As yet another example, other illumination scheme embodiments may extend a bit outside the vertical blanking period in order to trade off some image distortion with increased integration time. Still other embodiments will be apparent to those skilled in the art and having the benefit of the present disclosure.

Figure 12:
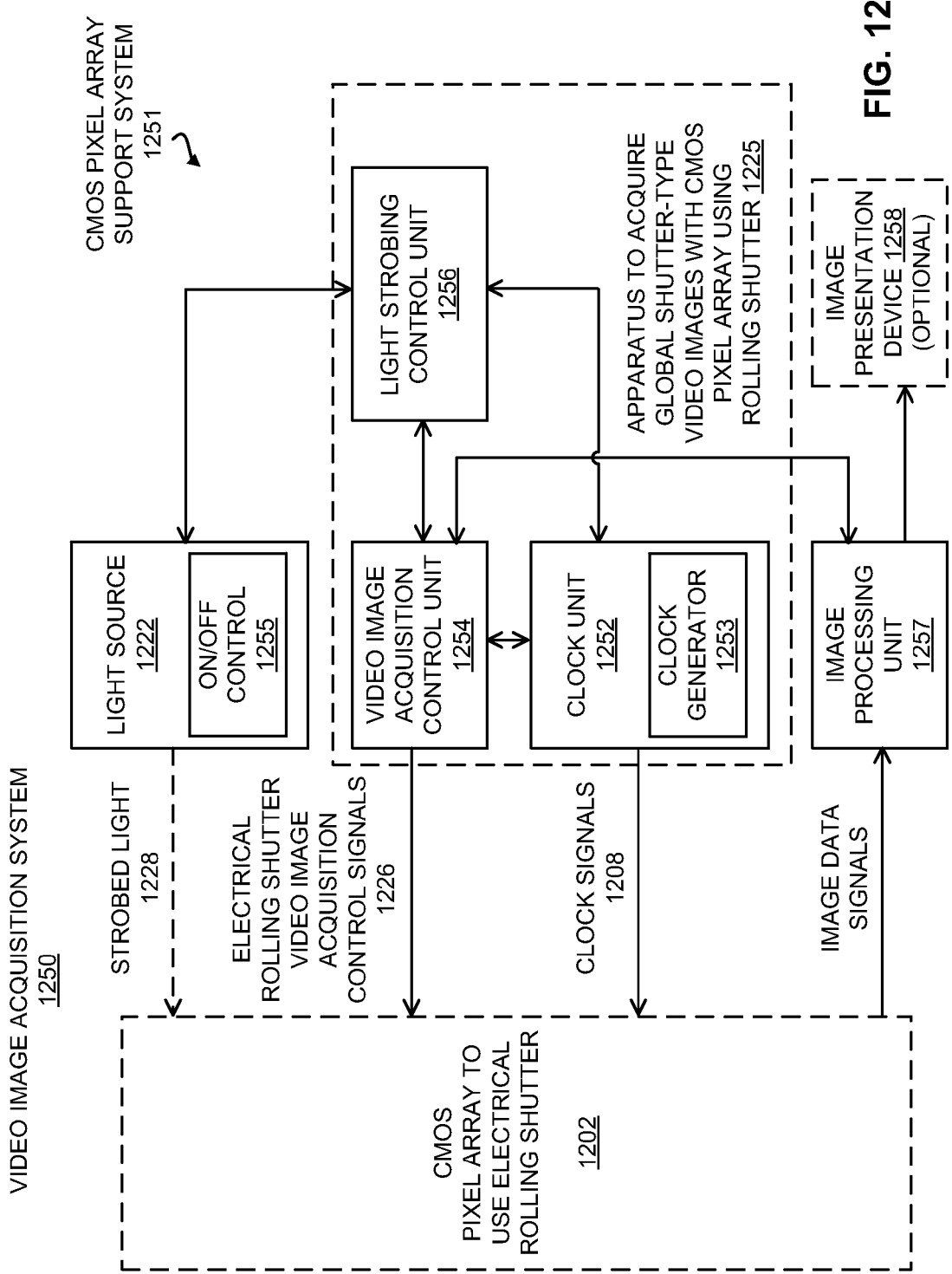
FIG. 12 is a block diagram of an embodiment of a video image acquisition system that is operable to acquire global shutter type video images with a CMOS pixel array that is to use an electrical rolling shutter.

FIG. 12 is a block diagram of an embodiment of a video image acquisition system 1250 that is operable to acquire global shutter-type video images with a CMOS pixel array that is to use an electrical rolling shutter. The video image acquisition system 1250 includes the CMOS pixel array 1202 that is to use the electrical rolling shutter. A CMOS pixel array support system 1251 is coupled with, and is operable to support the CMOS pixel array 1202. In some embodiments, the video image acquisition system 1250 may represent an endoscope video image acquisition system, although the scope of the invention is not so limited. For example, the video image acquisition system may represent the endoscope video image acquisition system 515 of FIG. 5, or an entirely different one.

The CMOS pixel array support system 1251 includes an apparatus 1225 that is operable to acquire global shutter-type images with the CMOS pixel array using the electrical rolling shutter. The apparatus 1225 includes a clock unit 1252. The clock unit includes a clock signal generator 1253. The clock unit is operable to provide clock signals 1208 to the CMOS pixel array. The apparatus 1225 also includes a video image acquisition control unit 1254. The video image acquisition control unit is operable to provide electrical rolling shutter video image acquisition control signals 1226 to the CMOS pixel array to control the CMOS pixel array to acquire video images using an electrical rolling shutter. The signals for each video image are operable to reset each row of pixels of the CMOS pixel array sequentially, and one row at a time, from a first row to a last row, and then to read each row of pixels of the CMOS pixel array sequentially, and one row at a time, from the first row to the last row. In some embodiments, the signals are such that the resetting of the last row of a given image frame is to be performed before the reading of the first row of the given image frame. The signals define, between each pair of consecutive video images, a vertical blanking period between the reading of the last row of pixels of a prior video image frame and the readout of the first row of pixels of a subsequent video image frame. The video image acquisition control unit is coupled with the clock unit. In some embodiments, the signals may be operable to generate the reset-readout blocks for FIG. 10 and/or FIG. 11. Alternatively, the signals may be operable to generate different reset-readout blocks. The video image acquisition control unit may be implemented in hardware (e.g., circuitry), software, firmware, or a combination thereof.

The apparatus 1225 also includes a light strobing control unit 1256. The light strobing control unit 1256 is coupled with a light source 1222, the video image acquisition control unit 1254, and the clock unit 1252. The light strobing control unit 1256 is operable to provide light strobing control signals to the light source 1222 to control the light source to provide strobed light 1228 to the CMOS pixel array. In some embodiments, the light strobing control unit may be operable to control the light source to provide substantial light during at least a portion of each of the vertical blanking periods, and control the light source not to provide substantial light between: (1) the readout of the first and last rows of pixels during the previous video image frames before the vertical blanking periods; and (2) the readout of the first and last rows of pixels during the subsequent video image frames after the vertical blanking periods. The light strobing control unit may be implemented in hardware (e.g., circuitry), software, firmware, or a combination thereof.

As shown, in some embodiments, the light source 1222 has an on/off control 1255 to allow the light source to be turned on and off multiple or many times in succession by the light strobing control signals in order to provide the strobed light. In some embodiments, the on/off control may switch on and off an LED, laser, lamp, bulb, or other light emission device of the light source. Alternatively, the light from the light source may be blocked/not blocked, reflected/not reflected, diverted/not diverted, or otherwise provided/not provided. As will be mentioned further below, in some embodiments, the light strobing control unit may also include a light intensity control unit (not shown) to control intensity (e.g., to turn up or dim down) of light provided by the light source, although this is not required. Also, in other embodiments, the light source may not be included in the CMOS pixel array support system as previously described.

The video image acquisition control unit 1254, the clock unit 1252, and the light strobing control unit 1256 may coordinate the strobed light 1228, the electrical rolling shutter video image acquisition control signals 1226, and the clock signals 1208, so that illumination occurs only within the vertical blanking periods. In some embodiments, the light strobing control unit 1256 generates the light strobing control signals based on information from the video image acquisition control unit 1254 and/or the clock unit 1252. In some embodiments, the light strobing control signals are timed relative to the electrical rolling shutter video image acquisition control signals 1226 and/or the clock signals 1208. In one embodiment, such as when the image sensor is relatively small, some pads may be used in a multitask fashion for both control and clock signals, although this is not required.

The CMOS pixel array support system 1251 also includes an image processing unit 1257. The image processing unit may be substantially conventional and may process image data signals received from the image sensor in any of various conventional ways that do not limit the scope of the invention. An optional image presentation device 1258 is also shown. The image presentation device may present images from the image processing unit to a user. Examples of suitable image presentation devices include, but are not limited to, display devices, printers, faxes, and other image presentation devices known in the arts. Alternatively, rather than being presented to a user, the images may be stored (e.g., in a memory) or otherwise preserved.

Figure 13:
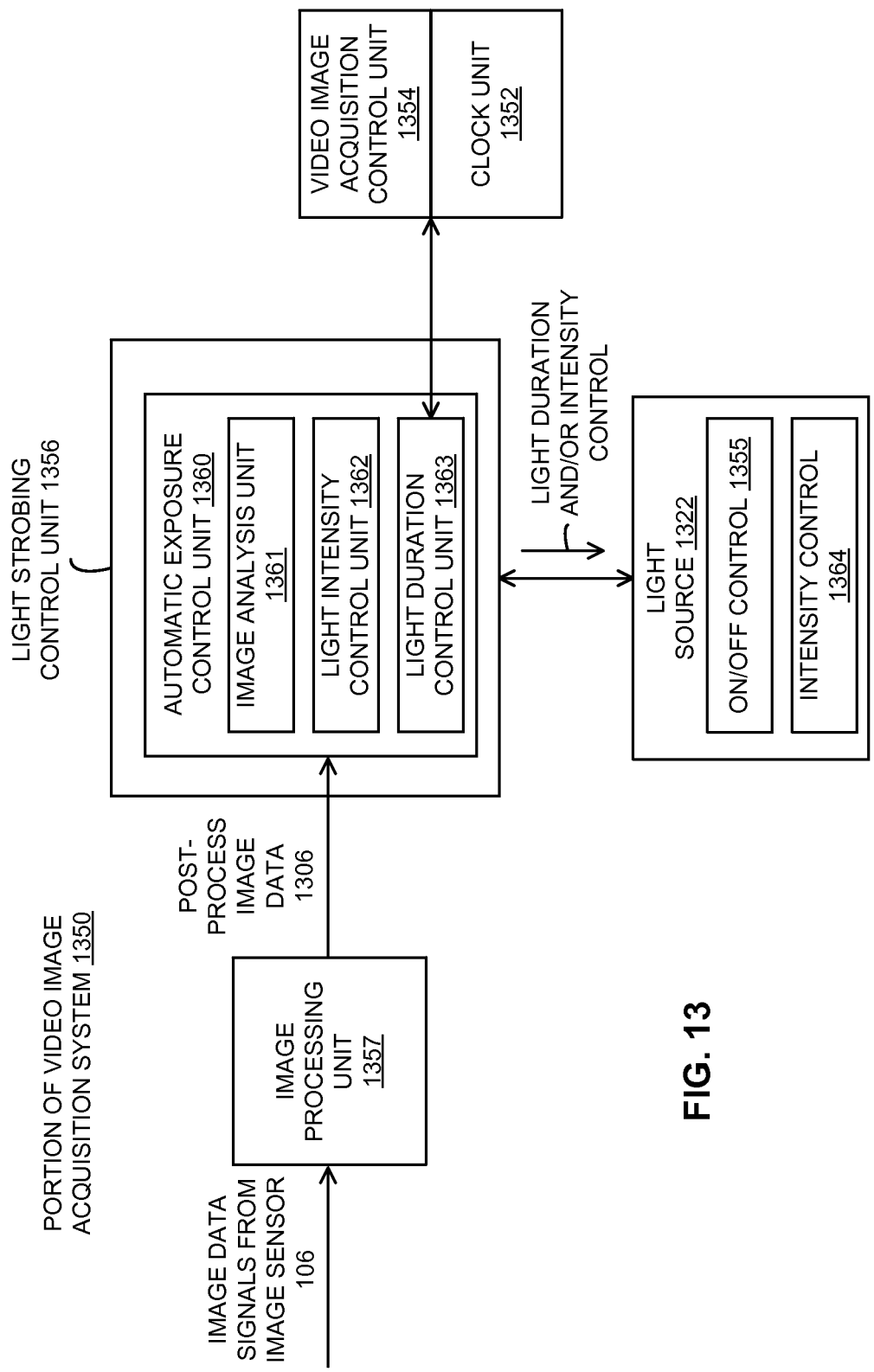
FIG. 13 is a block diagram of an embodiment of a portion of a video image acquisition system having an automatic exposure control unit.

FIG. 13 is a block diagram of an embodiment of a portion of a video image acquisition system 1350 having an automatic exposure control unit 1360. In various embodiments, the portion 1350 may be included in the endoscope video image acquisition system 515 of FIG. 5, the video image acquisition system 1250 of FIG. 12, or a different video image acquisition system.

The portion of the video image acquisition system 1350 includes an image processing unit 1357. The image processing unit may receive image data signals 106 (e.g., from a CMOS pixel array 102 or image sensor 101 of FIG. 1). The image processing unit may process the image data signals. Conventional ways of processing the image data signals are suitable.

The automatic exposure control unit 1360 may receive post-process image data 1306 from the image processing unit 1357. In the illustrated embodiment, the automatic exposure control unit 1360 is shown as being part of a light strobing control unit 1356. Alternatively, the automatic exposure control unit may be separate from the light strobing control unit. The automatic exposure control unit is operable to automatically or autonomously control and adjust the amount of light illumination provided by a light source 1322 based at least in part on the post-process image data 1306. In some embodiments, the automatic exposure control unit may provide feedback control based on information from the already acquired image data. In other embodiments, the automatic exposure control unit may provide feedforward control. In still other embodiments, the automatic exposure control unit may provide both feedback and feedforward control or other types of control. Advantageously, such an automatic exposure control unit may help to improve the quality of images acquired by the video image acquisition system by adjusting the amount of light illumination so that the images are of appropriate brightness, etc.

The automatic exposure control unit 1360 includes an image analysis unit 1361. The image analysis unit 1361 is operable to analyze the received image data 1306. In some embodiments, the analysis may include analyzing exposure-dependent features of the image data that depend on the amount of exposure. A few examples of suitable exposure-dependent features include, but are not limited to, average brightness, brightness distribution, brightness histogram, etc. It will be appreciated by those skilled in the art and having the benefit of the present disclosure that various other features that allow one to determine whether the image is of appropriate brightness may also or alternatively be used. In some embodiments, the image analysis unit and/or the automatic exposure control unit may include a predetermined standard amount of exposure, and may be operable to compare this predetermined standard amount of exposure with the amount of exposure obtained from the received image data. By way of example, the preexisting standard amount of exposure may represent a predetermined desired amount of exposure (e.g., a desired average or minimum brightness of the image).

The automatic exposure control unit 1360 may control the light source 1322 to adjust the amount of light illumination based on the analysis of the image data 1306. In general the amount of light exposure or illumination of the CMOS pixel array in the dark environment depends primarily on (1) the intensity of the light provided by the light source; and (2) the duration of the light provided by the light source. For example, the amount of light exposure or illumination may be approximated by the product of the light intensity times the duration of light. In some embodiments, either or both of the light intensity and/or the duration of the light provided by the light source may be adjusted in order to adjust the amount of illumination or light exposure, as further disclosed below.

As shown, in some embodiments, the automatic exposure control unit includes a light intensity control unit 1362 that is operable to control adjustment of an intensity of the light from the controlled light source during a vertical blanking period for an image frame subsequent to a present image frame, and a light duration control unit 1363 that is operable to control adjustment of duration of the light from the controlled light source during a vertical blanking period for an image frame subsequent to a present image frame. In other embodiments, the automatic exposure control unit may include either, but not both, of these units.

In some embodiments, the duration of light may be controlled by the light duration control unit 1363 exerting control over an on/off control 1355 of the light source 1322, although this is not required. In some embodiments, the light duration control unit 1363 may communicate with the light strobing control unit 1356 to have the light strobing control unit control the on/off control. In some embodiments, the duration of the vertical blanking period may be changed (e.g., increased or decreased). The light duration control unit may also communicate or signal a video image acquisition control unit 1354 and/or a clock unit 1352 to coordinate timing.

Figure 15:
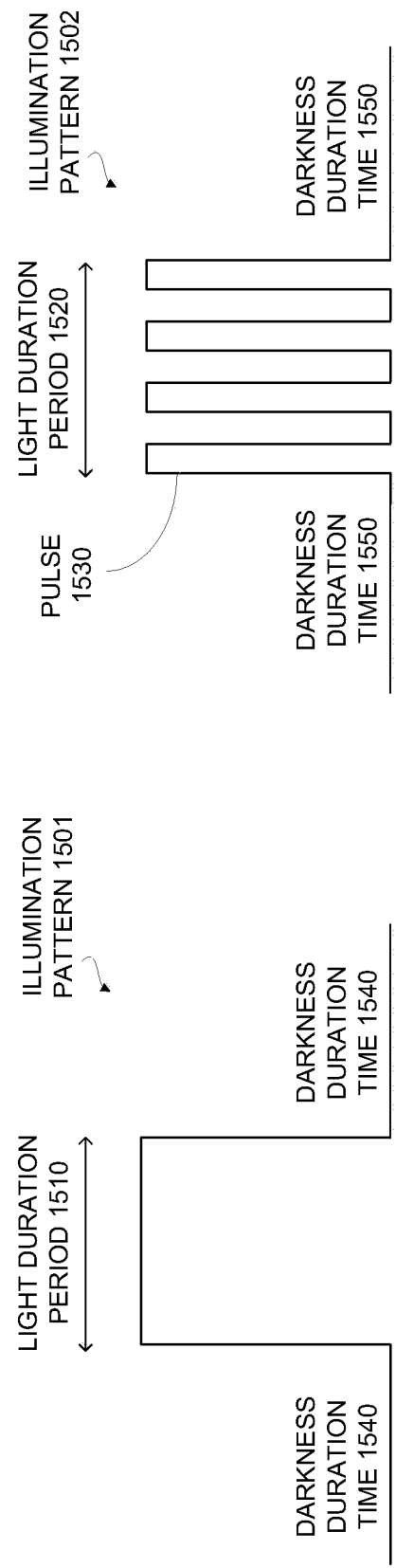
FIG. 15 illustrates an embodiment to reduce light duration period by providing light in pulses.

In some embodiments, to reduce the duration of the light from the controlled light source 1322, a continuous light duration period may be broken down into a series of shorter light duration periods. FIG. 15 shows two illumination patterns. The light duration period 1510 of the illumination pattern 1501 at the left side of FIG. 15 is continuous. To reduce the duration of light, instead of providing continuous light, the light duration control unit 1363 may control the light source 1322 to provide light in a series of pulses 1530, shown as the illumination pattern 1502 at the right side of FIG. 15. The resulting light duration period 1520 of pattern 1502 contains less illumination time than the light duration period 1510 of pattern 1501. The darkness duration times 1540 and 1550 are substantially the same for both illumination patterns.

Referring again to FIG. 13, in some embodiments, the light intensity may be controlled by the light intensity control unit 1362 controlling intensity control 1364 of the light source 1322. By way of example, this may involve changing a voltage, a current, a power, a combination thereof, or other electrical input to the light source.

To further illustrate certain concepts, consider a few illustrative examples. In one example, if the image data indicates that the image is about half as bright as desired, then the light intensity may be controlled to be about twice as large for a subsequent image frame. As another example, if the image data indicates that the image is about half as bright as desired, then the duration of light may be controlled to be about twice as long for a subsequent image frame. In other examples both duration and intensity together may be changed to achieve the desired brightness. As yet another example, if the brightness is sufficiently close to the desired brightness, but the video images are too choppy as analyzed by the image analysis unit, then the frame rate may be increased. Decreasing the frame rate generally also decreases the vertical blanking period, which in some cases may decrease the duration of light exposure or illumination. If such is the case for the embodiment, then the light intensity may be increased to account for the decrease in light exposure duration so that the amount of light exposure remains approximately the same.

Figure 14:
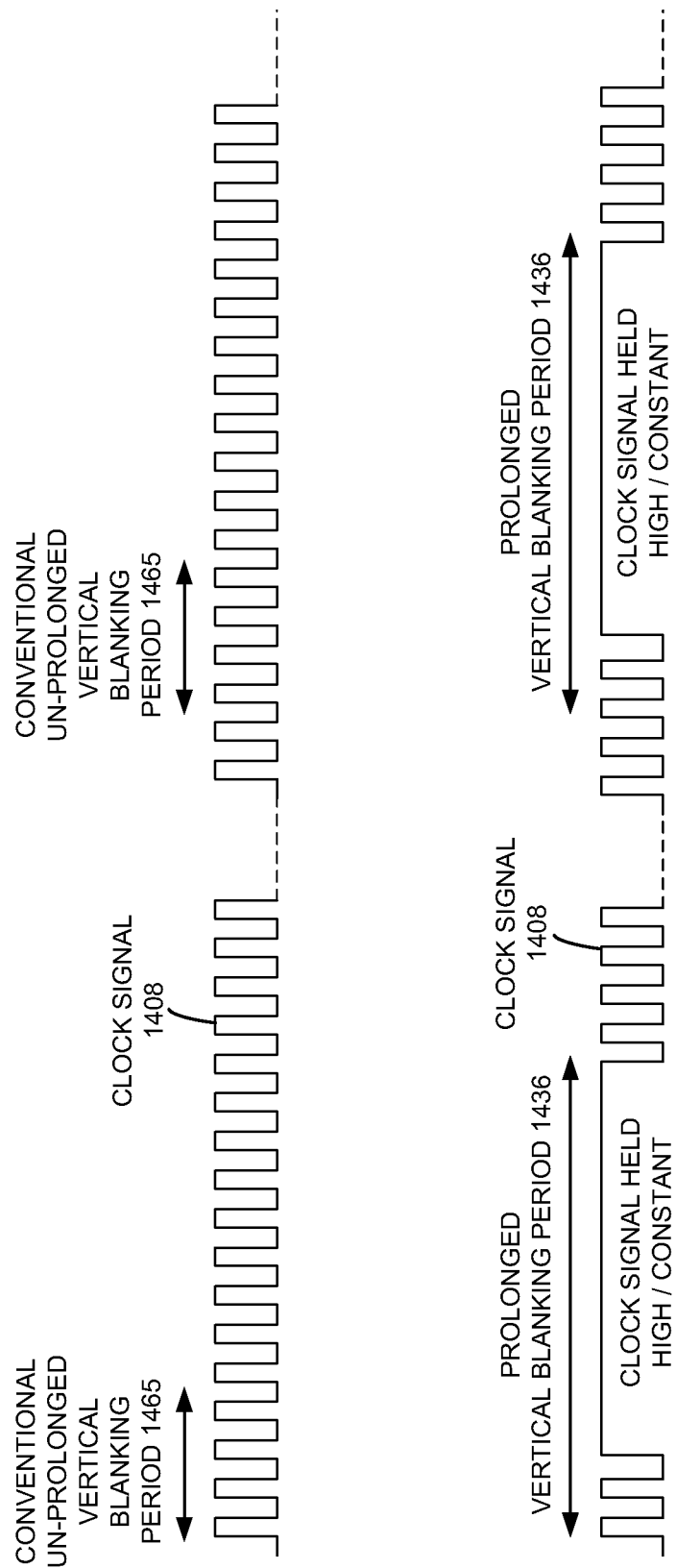
FIG. 14 illustrates conventional un-prolonged vertical blanking periods, an embodiment of prolonged vertical blanking periods, and an embodiment of an approach for prolonging the prolonged vertical blanking periods by holding a clock signal at a constant level during the prolonged vertical blanking periods.

FIG. 14 illustrates both an embodiment of conventional, regular, un-prolonged vertical blanking periods 1465, and an embodiment of prolonged vertical blanking periods 1436. Also disclosed in FIG. 14 is an embodiment of an approach for prolonging the prolonged vertical blanking periods by holding a clock signal 1408 high (i.e., at a constant level) during at least a portion of each of the prolonged vertical blanking periods. The prolonged vertical blanking periods have a longer duration in time than the regular, un-prolonged vertical blanking periods. In various example embodiments, the prolonged vertical blanking periods are at least 110%, at least 120%, at least 150%, at least 200%, or even longer than the regular, un-prolonged vertical blanking periods.

The clock signal for the conventional un-prolonged vertical blanking periods continuously switches between high and low levels at the same clock cycle rate over the entire period of time. In contrast, the clock signal for the prolonged vertical blanking periods does not continuously switch between high and low levels at the same clock cycle rate over the entire period of time shown. Rather, during at least a portion of the vertical blanking periods, the clock signal is held at a constant level (in this case, a high level) for a period of time corresponding to multiple clock cycles. This prolongs the vertical blanking periods. In the illustrated embodiment, the clock signal is held high, although alternatively the clock signal may be held low. Holding the clock signal at the constant level effectively stops the clock and prolongs the vertical blanking periods for the duration that the clock signal is held constant. In some embodiments, in addition to prolonging the vertical blanking periods, the frame rate may be commensurately reduced. In one particular example embodiment, the un-prolonged vertical blanking periods may be approximately 30 ms in a video sequence having approximately 30 frames/sec, whereas the prolonged vertical blanking periods may be approximately 60 ms (i.e., approximately twice as long) in a video sequence having approximately 15 frames/sec (i.e., approximately half the frame rate).

Figure 16A:
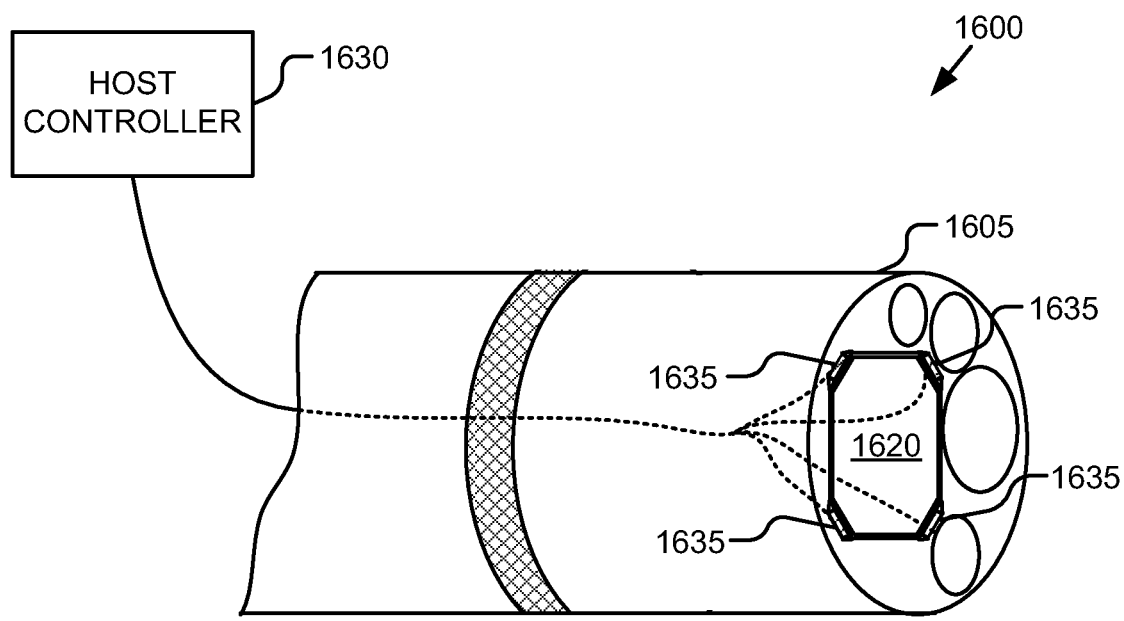
FIGS. 16A-D show embodiments of endoscopes that include light sources and CMOS pixel arrays that are to use electrical rolling shutters.
Figure 16B:
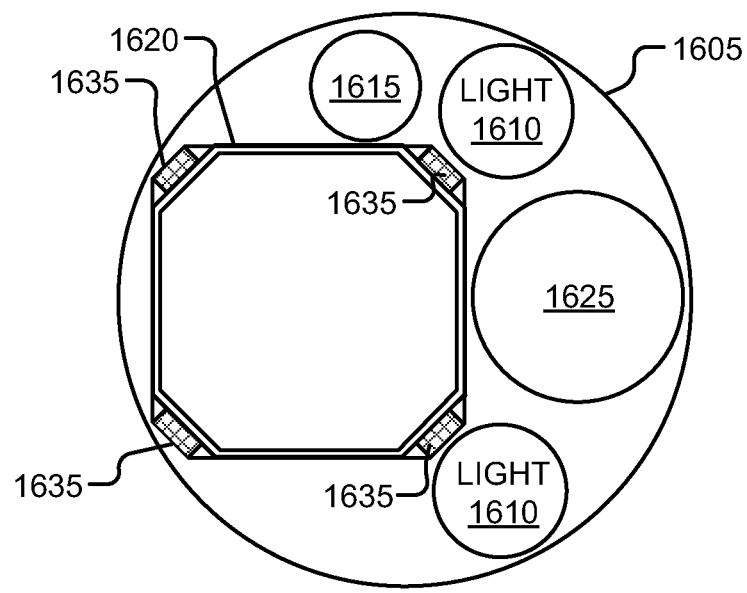

FIGS. 16A and 16B are diagrams of an endoscope 1600 including an image sensor 1620, in accordance with an embodiment of the disclosure. Endoscope tip 1605 is for inserting, often into a cavity of a subject of an endoscope examination, to provide imaging data. In FIG. 16A, image sensor 1620 is disposed on endoscope tip 1605. FIG. 16A also illustrates host controller 1630 coupled to image sensor 1620 via four terminals 1635. Image sensor 1620 may include a CMOS pixel array to use electrical rolling shutter, as disclosed above as CMOS pixel arrays 502 and 1202 in FIGS. 5 and 12 respectively. Host controller 1630 may be any of the previously discussed controllers including endoscope base station 516 in FIG. 5, and apparatus 1225 and unit 1251 in FIG. 12.

FIG. 16B is a front view of endoscope tip 1605 that includes lights 1610, and accessories 1615 and 1625. Endoscope tip 1605 may be used in the medical field or otherwise. Accessories 1615 and 1625 may include suction or forceps utilities. The reduction in the number of terminals 1635 included on image sensor 1620 may allow for the overall size of image sensor 1620 to be reduced, and in turn, the overall size of endoscope tip 1605 may be reduced. In addition, a reduced size image sensor 1620 may allow for improved, larger, or additional accessories to fit within endoscope tip 1605. Any of these improvements may increase the success rate of the action being performed with the endoscope (such as surgery).

Figure 16C:
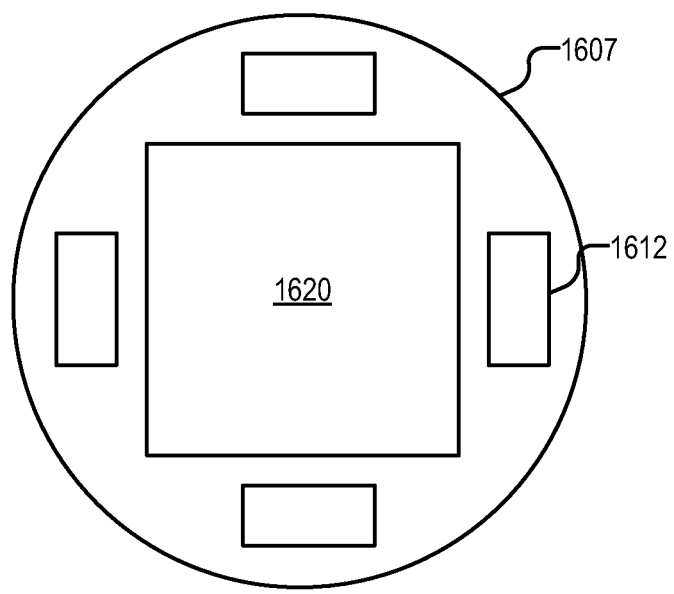
Figure 16D:
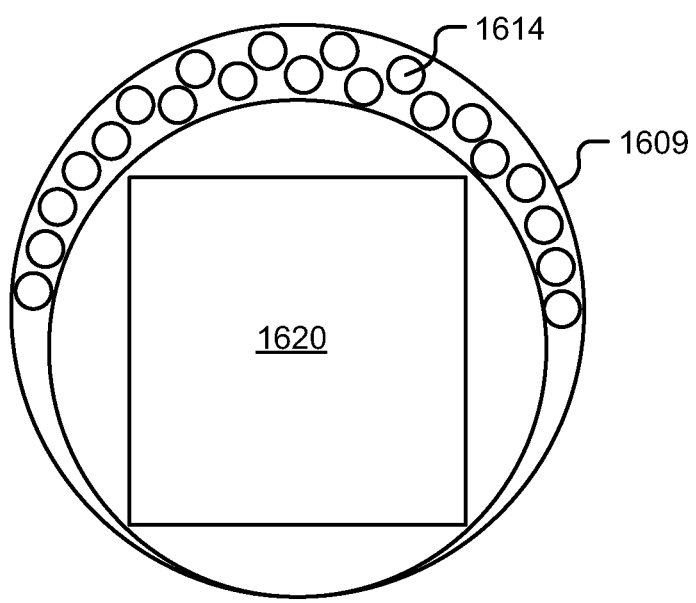

FIG. 16C is a top view of an endoscope tip 1607 that includes image sensor 1620 and lights 1612. This is a type of endoscope that is used for diagnostic purposes, thus it includes relatively large areas for lighting. In this embodiment, four LED lights 1612 surround image sensor 1620. In another embodiment, shown in FIG. 16D, an area around image sensor 1620 of endoscope tip 1609 is occupied by a multitude of optic fibers 1614, which is used to provide lighting at endoscope tip 1609.

Embodiments have been described in conjunction with endoscope video imaging systems. However, the scope of the invention is not so limited. Other embodiments are suitable for boroscopes, hydraulic pigs, other monitoring probes, and other inspection devices for engine, industrial, pipeline, and other applications. There is no requirement of two-part form factor in which a CMOS pixel array is separated from (e.g., connected by cable(s) to) a support system. Other embodiments may be used in single form factor video image acquisition systems, such as, for example, standard digital cameras. Embodiments have been described above in conjunction with a moving CMOS pixel array and a stationary object being imaged. However, other embodiments are applicable to a stationary CMOS pixel array and a moving object being imaged. Accordingly, embodiments pertain to a wide variety of different types of devices having CMOS pixel arrays that are to be used in dark or relatively dark environments when there is relative movement between the CMOS pixel array and an object being imaged (e.g., the CMOS pixel array and/or the object is moving).

In the description and claims, the terms "coupled" and/or "connected," along with their derivatives, have be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still co-operate or interact with each other.

In the description and claims, the term "logic" has been used. As used herein, the term logic may include hardware (e.g., circuitry), firmware, software (e.g., instructions stored on a tangible storage medium), or various combinations thereof. Examples of logic include integrated circuitry, application specific integrated circuits, analog circuits, digital circuits, programmed logic devices, memory including instructions, etc. In some embodiments, the logic may include at least some circuitry (e.g., transistors, active circuit elements, passive circuit elements, integrated circuitry, etc.).

In the description above, specific details have been set forth in order to provide a thorough understanding of the embodiments. However, other embodiments may be practiced without some of these specific details. The scope of the invention is not to be determined by the specific examples provided above but only by the claims below. All equivalent relationships to those illustrated in the drawings and described in the specification are encompassed within embodiments. In other instances, well-known circuits, structures, devices, and operations have been shown in block diagram form or without detail in order to avoid obscuring the understanding of the description.

Where multiple components have been shown and described, in some cases, these multiple components may optionally be integrated into one component. Where a single component has been shown and described, in some cases, this single component may be separated or divided into two or more components. In the illustrations lines (e.g., arrows) are used to show connections and couplings.

Certain methods disclosed herein have been shown and described in a basic form, although operations may optionally be added to and/or removed from the methods. In addition, a particular order of the operations may have been shown and/or described, although alternate embodiments may perform certain operations in different order, combine certain operations, overlap certain operations, etc.

One or more embodiments include an article of manufacture (e.g., a computer program product) that includes a machine-readable medium. The medium may include a mechanism that provides (e.g. stores) information in a form that is readable by a machine. The machine-readable medium may provide, or have stored thereon, a sequence of instructions that if executed by the machine causes or results in the machine performing operations and/or methods disclosed herein. Examples of suitable machines include, but are not limited to, endoscope base stations, video image acquisition systems, digital video cameras, and other video image acquisition systems having CMOS pixel arrays, computer systems, electronic devices having processors, etc.

In one embodiment, the machine-readable medium may include a tangible non-transitory machine-readable storage media. For example, the tangible non-transitory machine-readable storage media may include a floppy diskette, an optical storage medium, an optical disk, a CD-ROM, a magnetic disk, a magneto-optical disk, a read only memory (ROM), a programmable ROM (PROM), an erasable-and-programmable ROM (EPROM), an electrically-erasable-and-programmable ROM (EEPROM), a random access memory (RAM), a static-RAM (SRAM), a dynamic-RAM (DRAM), a Flash memory, a phase-change memory, or a combinations thereof. The tangible medium may include one or more solid materials, such as, for example, a semiconductor material, a phase change material, a magnetic material, etc.

Reference throughout this specification to "one embodiment," "an embodiment," "one or more embodiments," "some embodiments," for example, indicates that a particular feature may be included in the practice of the invention but is not necessarily required to be. Similarly, in the description various features are sometimes grouped together in a single embodiment, Figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects lie in less than all features of a single disclosed embodiment. Thus, the claims following the Detailed Description are hereby expressly incorporated into this Detailed Description, with each claim standing on its own as a separate embodiment of the invention.

What is claimed is:

1. A video producing method comprising:
   introducing a complementary metal oxide semiconductor (CMOS) pixel array into a dark environment that has substantially no ambient light; and
   acquiring a plurality of image frames, including a first image frame and a second image frame of an object in the dark environment with the CMOS pixel array, wherein acquiring the plurality of image frames comprises:

during the first image frame:
  resetting each row of pixels of the CMOS pixel array sequentially, and one row at a time, from a first row to a last row; and
  reading each row of pixels of the CMOS pixel array sequentially, and one row at a time, from the first row to the last row,
  wherein the resetting of the last row during the first image frame is performed before the reading of the first row during the first image frame;
during the second image frame:
  resetting each row of pixels of the CMOS pixel array sequentially, and one row at a time, from the first row to the last row; and
  reading each row of pixels of the CMOS pixel array sequentially, and one row at a time, from the first row to the last row wherein the resetting of the last row during the second image frame is completed before the reading of the first row during the second image frame;
controlling a light source to substantially illuminate the dark environment during a portion of a vertical blanking period, wherein the vertical blanking period is between the reading of the last row of pixels during the first image frame and the reading of the first row of pixels during the second image frame, and wherein the portion of the vertical blanking period is between the resetting of the last row of pixels during the second image frame and the reading of the first row of pixels during the second image frame; and
controlling the light source to not substantially illuminate the dark environment:
  (a) between the reading of the first row of pixels and the reading of the last row of pixels during the first image frame; and
  (b) between the reading of the first row of pixels and the reading of the last row of pixels during the second image frame.

2. The method of claim 1, wherein acquiring the plurality of image frames in the dark environment comprises strobing light from the light source, wherein the strobing includes:
  substantially illuminating the dark environment during a plurality of sequential vertical blanking periods; and
  not substantially illuminating the dark environment at times that are not within the plurality of sequential vertical blanking periods.

3. The method of claim 1, wherein introducing the CMOS pixel array into the dark environment comprises inserting an endoscope probe having the CMOS pixel array into a subject of endoscope examination.

4. The method of claim 3, further comprising moving the endoscope probe having the CMOS pixel array within the subject of endoscope examination, and wherein acquiring the plurality of image frames comprises acquiring the plurality of image frames while moving the endoscope probe having the CMOS pixel array within the subject of endoscope examination.

5. The method of claim 1, further comprising:
analyzing an acquired image frame; and
based on the analysis of the acquired image frame, adjusting at least one of:
  (a) an intensity of light from the light source during a subsequent vertical blanking period; and
  (b) a time period during which the light from the light source is used to illuminate the dark environment during the subsequent vertical blanking period.

6. The method of claim 1, further comprising prolonging the vertical blanking period, including suspending cycles of a clock signal, which is applied during the vertical blanking period, for a period of time corresponding to a plurality of the cycles.

7. The method of claim 1, further comprising prolonging a subsequent vertical blanking period after the second image frame, wherein the subsequent vertical blanking period has a longer duration than the vertical blanking period between the first image frame and the second image frame.

8. The method of claim 1, wherein controlling the light source to substantially illuminate the dark environment comprises switching on a light emission device during the vertical blanking period, and wherein controlling the light source to not substantially illuminate the dark environment comprises switching off the light emission device before and after the vertical blanking period between the first image frame and the second image frame.

9. The method of claim 1, wherein, after the reading of the first row of pixels of the first image frame, the resetting of the first row of pixels of the second image frame is performed within a time that is sufficient to read no more than about an initial 5% of the rows of pixels of the CMOS pixel array.

10. The method of claim 1, wherein the acquiring the plurality of image frames comprises concurrently accumulating photoelectric generated charges in at least about 90% of the rows of pixels of the CMOS pixel array over a same period of time.

11. A video image acquisition system comprising:
  a complementary metal oxide semiconductor (CMOS) pixel array including an electrical rolling shutter;
  a clock unit including a clock signal generator, wherein the clock unit is operable to provide clock signals to the CMOS pixel array;
  an image acquisition control unit that is operable to provide control signals to the CMOS pixel array to control the CMOS pixel array to acquire video images,
  wherein the control signals for each video image are operable to reset each row of pixels of the CMOS pixel array sequentially, and one row at a time, from a first row to a last row,
  wherein the control signals for each video image are operable to read each row of pixels of the CMOS pixel array sequentially, and one row at a time, from the first row to the last row,
  wherein the resetting of the last row of a given image frame is to be performed before the reading of the first row of the same given image frame, and
  wherein the image acquisition control unit is operable to provide control signals that define, between each pair of consecutive video images, a vertical blanking period between the reading of the last row of pixels of a prior video image and the reading of the first row of pixels of a subsequent video image; and
  a light strobing control unit that is operable to control a light source to:
  substantially provide light during a portion of each of the vertical blanking periods, wherein the portion of the vertical blanking period is between the resetting of the last row of pixels during the prior video image frame and the reading of the first row of pixels during the subsequent image frame; and
  not substantially provide light between (a) the reading of the first and last rows of pixels during the previous video images and (b) the reading of the first and last rows of pixels during the subsequent video images.

12. The system of claim 11, further comprising an exposure control unit operable to analyze an acquired video image, and based on the analysis, is operable to adjust at least one of: (a)

an intensity of light that is to be provided from the light source during a subsequent vertical blanking period; and (b) a time period during which the light is to be provided from the light source during a subsequent vertical blanking period.

13. The system of claim 11, wherein the image acquisition control unit is operable to provide control signals that define a regular vertical blanking period and a prolonged vertical blanking period, wherein the prolonged vertical blanking period has a greater duration in time than the regular vertical blanking period.

14. The system of claim 11, further comprising a unit operable to prolong the vertical blanking period by suspending cycles of a clock signal, which is applied during the prolonged vertical blanking period, for a period of time corresponding to a plurality of the cycles.

15. The system of claim 11, implemented in a base station for an endoscope, wherein the base station comprises a connector interface that is operable to allow the endoscope having the CMOS pixel array to be connected;

wherein the clock unit is operable to provide the clock signals to the endoscope through the connector interface; and wherein the image acquisition control unit is operable to provide the control signals to the endoscope through the connector interface.

16. The system of claim 11, wherein, after the reading of the first row of pixels of the prior video image, the video image acquisition control unit is operable to provide control signals to cause the resetting of the first row of pixels of the subsequent video image to be performed within a time that is sufficient to read no more than about an initial 5% of the rows of pixels of the CMOS pixel array.

17. The system of claim 11, wherein, for the given image frame, at least about 90% of the rows of pixels of the CMOS pixel array accumulate photoelectric generated charges over a same total period of time.

18. The system of claim 11, further comprising the light source, wherein the light source comprises a light emission device.

19. The system of claim 18, wherein the light strobing control unit is operable to switch on and off the light emission device of the light source.

20. A video producing method comprising:
inserting an endoscope probe having a complementary metal oxide semiconductor (CMOS) pixel array that uses an electrical rolling shutter into a subject of endoscope examination;
moving the endoscope probe within the subject;
acquiring a sequence of image frames with the CMOS pixel array, while moving the endoscope probe within the subject, and while using the electrical rolling shutter, wherein acquiring the sequence of image frames includes defining a vertical blanking period between reading a last row of pixels of a first image frame and reading a first row of pixels of a subsequent image frame; and
strobing light from a light source so that the light is substantially on during a portion of each the vertical blanking period between consecutive image frames and substantially off within each image frame between (a) a reading of the first and last rows of pixels during the first image frame and (b) a reading of the first and last rows of pixels during the subsequent image frame while reading out rows of pixels of the CMOS pixel array,
wherein the portion of the vertical blanking period is between a resetting of a last row of pixels of the CMOS pixel array during a first image frame and the reading of the first row of pixels during the subsequent image frame.

21. The method of claim 20, further comprising:
analyzing a given image frame; and
based on the analysis of the given image frame, adjusting at least one of:
(a) an intensity of light from the light source that is to be used during a vertical blanking period subsequent to the given image frame; and
(b) a time period during which the light from the light source is to be on during the vertical blanking period subsequent to the given image frame.

22. The method of claim 20, further comprising prolonging the vertical blanking period subsequent to the given image frame, wherein the prolonged vertical blanking period has a longer duration than a vertical blanking period that precedes the given image frame.

23. The method of claim 22, wherein prolonging the vertical blanking period subsequent to the given image frame includes suspending cycles of a clock signal for a period of time corresponding to a plurality of the cycles.

* * * * *